United States Patent
Ching et al.

(10) Patent No.: US 7,335,477 B2
(45) Date of Patent: *Feb. 26, 2008

(54) **TRUNCATED RECOMBINANT MAJOR OUTER MEMBRANE PROTEIN ANTIGEN (R56) OF *ORIENTIA TSUTSUGAMUSHI* STRAINS KARP, KATO AND GILLIAM AND ITS USE IN ANTIBODY BASED DETECTION ASSAYS AND VACCINES**

(75) Inventors: Wei-Mei Ching, Bethesda, MD (US); Daryl J. Kelly, Newark, OH (US); Gregory A. Dasch, Stone Mountain, GA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/120,837

(22) Filed: Apr. 12, 2002

(65) Prior Publication Data

US 2003/0165523 A1    Sep. 4, 2003

Related U.S. Application Data

(63) Continuation-in-part of application No. 09/218,425, filed on Dec. 22, 1998, now Pat. No. 6,482,415.

(60) Provisional application No. 60/283,373, filed on Apr. 13, 2001, provisional application No. 60/068,732, filed on Dec. 24, 1997.

(51) Int. Cl.
G01N 33/53 (2006.01)
(52) U.S. Cl. .............. 435/7.1; 435/7.2; 435/7.22; 435/7.32; 435/7.9; 435/7.92; 435/7.93; 435/7.94; 435/7.95; 530/350
(58) Field of Classification Search ............ 435/7.1, 435/7.2, 7.22, 7.32, 7.9, 7.92, 7.93, 7.94, 435/7.95; 530/350
See application file for complete search history.

(56) References Cited

U.S. PATENT DOCUMENTS 5,439,808 A * 8/1995 Blake et al. .............. 435/69.1

OTHER PUBLICATIONS

Stover et al. Infect.Immun. 1990. 58(7): 2076-2084.*
Kim et al (J.Clin.Microbiol., 1993. 31(3): 598-605.*
Ohashi et al (Infect.Immun., 1989, 57(5): 1427-1431).*

* cited by examiner

*Primary Examiner*—Jennifer Graser
(74) *Attorney, Agent, or Firm*—Ning Yang; Joseph K. Hemby

(57) ABSTRACT

A recombinant, refolded non-fusion polypeptide expressed from a truncated r56 gene of the causative agent of scrub typhus, *Orientia tsutsugamushi* for the Karp, Kato and Gilliam strains has been produced. The invention is useful for detecting prior exposure to scrub typhus, screening for and/or identification of at least one infectious strain-similarity (i.e. a Karp-like, Kato-like or Gilliam-like strain) based on its strength of reaction toward a truncated protein and as a component in vaccine formulations and production of immune globulins for passive prophylaxis and immunity in subjects.

4 Claims, 7 Drawing Sheets

Figure 1:
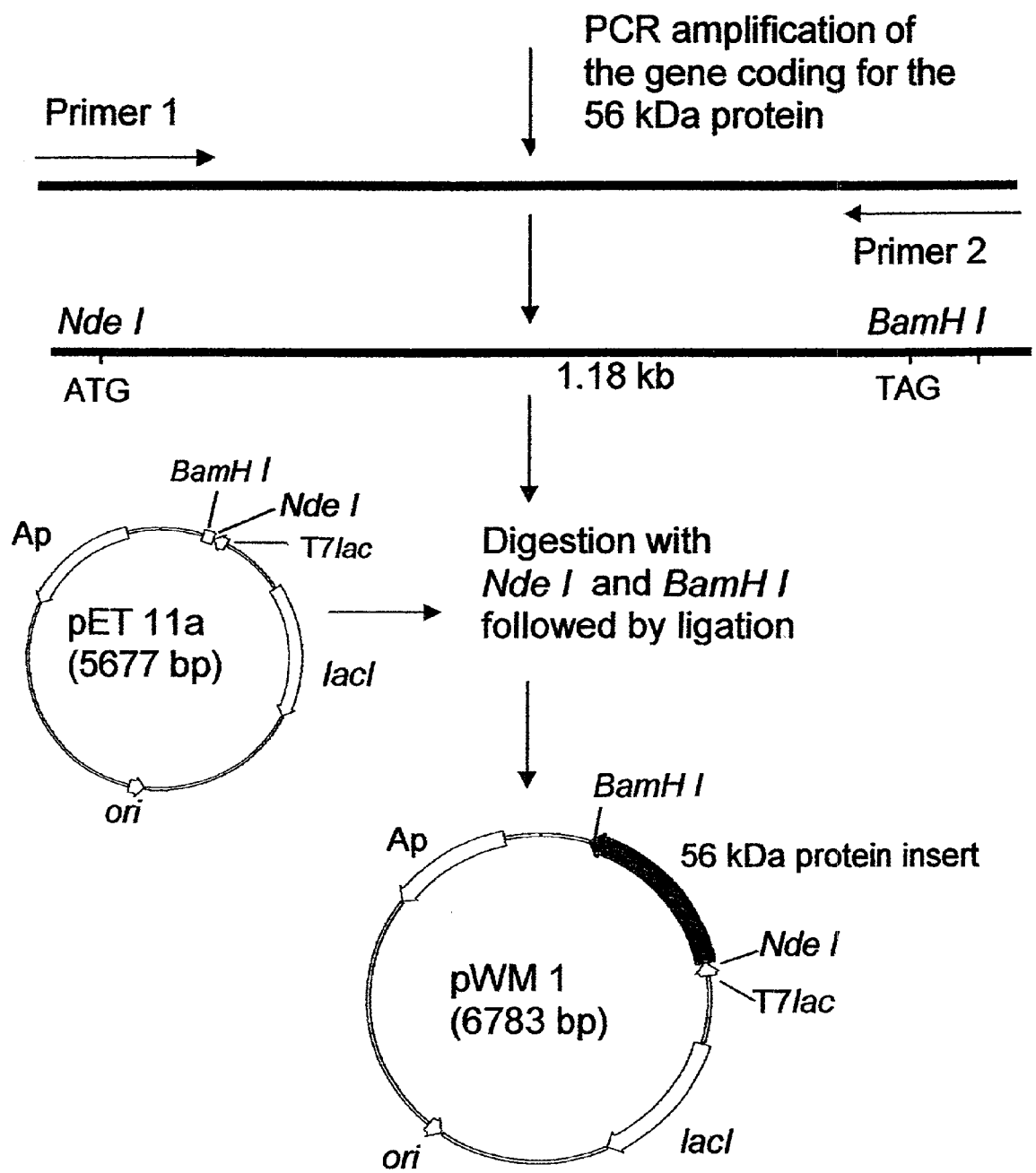

TRUNCATED RECOMBINANT MAJOR OUTER MEMBRANE PROTEIN ANTIGEN (R56) OF *ORIENTIA TSUTSUGAMUSHI* STRAINS KARP, KATO AND GILLIAM AND ITS USE IN ANTIBODY BASED DETECTION ASSAYS AND VACCINES

CROSS-REFERENCE

This is a Continuation-In-Part Application of application Ser. No. 09/218,425 filed Dec. 22, 1998 (now U.S. Pat. No. 6,482,415) which claims priority from U.S. Provisional Application No. 60/068,732 filed on Dec. 24, 1997 and U.S. Provisional No. 60/283,373 filed on Apr. 13, 2001.

BACKGROUND OF THE INVENTION

Some of the most dreadful pandemics in the history of mankind result from the rapid spread of infectious diseases caused by virulent pathogenic organisms. These disease states are often accompanied by other opportunistic infections (viral, protozoal, bacterial or parasitic) and/or diseases due to the compromised immune system of infected patients.

There is new evidence that new epidemics are emerging throughout the industrialized, developing and transitional countries of the world.

Today, the rates of reported cases of diseases are increasing in exponential proportions and clinical treatments currently available represent only marginal improvements in the management of health care in this area. The rapid increase in the number of infectious diseases ranges from alarming to out of control. Unless improved treatments are found the future outlook for the state of the world's health is dismal. The scientific community throughout the world is mindful of the long-felt need for effective ways to (1) substantially reduce, eliminate, neutralize and/or kill virulent pathogenic organisms or agents, (2) inhibit the proliferation of rapidly replicating abnormal (infected or altered) cells caused by pathogenic organisms, or agents such as a virus, bacteria, fungus, venom, pollen, protozoal, and mixtures thereof and (3) identify effective vaccines, preventive (prophylactic) and therapeutic treatments for patients, including humans. In response to the need to alleviate suffering and provide comfort to human life, the scientific community is searching for effective means to inhibit the growth of rapidly proliferating abnormal mammalian cells caused by pathogenic organisms within the genus *Rickettsia*, such as *O. tsutsugamushi* alone and/or in combination with others.

Scrub typhus, also referred to as chigger-borne rickettsiosis, mite-borne typhus, Japanese river fever, tropical or rural typhus or *tsutsugamushi* disease is an acute, febrile disease caused by infection with *Orientia* (formerly *Rickettsia*) *tsutsugamushi*. It accounts for up to 23% of all febrile episodes in endemic areas of the Asia-Pacific region (5). The disease is characterized by a rise in body temperature, skin rash and severe headaches. This disease may affect the nervous system, with clinical manifestations such as delirium, stupor and muscle fibrillation. The death rate varies from 1 to 60% depending on the geographical regions. Scrub typhus, transmitted to mammals (including humans and cattle) through the bite of tiny trobiculid mites (arthropods) is particularly high in South-East Asia, Korea, Russia, Australia, China, Japan and India. The incidence of disease has increased in some countries during the past several years (6).

The causative organism is transmitted to human through the bite of tiny trobiculid mites. The organisms are found throughout the mite's body, but the highest number occurs in the salivary glands. When the mites feeds on mammals, including cattle, rodents or humans, the disease causing organisms are transmitted from the mite to the invertebrate host (subject). Srub typhus infections are usually found in people engaged in activities that bring them inadvertently in contact with mite-infested habitats or any invertebrate host-carrier of these anthropods. These hosts may include domesticated, non-domesticated or farm animals, such as cattle or rodents. These hosts may be carrying mites which have not begun to feed on them. In this case, when the host is cattle, the live mites can be transferred from cattle to people. Individuals particularly susceptiable include butchers, meat-workers, animal-farm workers and others engaged in outdoor activities. These persons could be infected by coming into contact with these mite-carrying animals. Additionally, rodents are capable of carrying and spreading infected mites to people in populated areas.

Only larval *Leptotrombidium* mites feed on vertebrate hosts. The larval mites acquire *O. tsutsugama* through their female parent. This type of pathogen reception is called "transovarial transmission."

Once transmitted to the host, the organism incubates for about 10 to 12 days. From 5 to 8 days after infection, a dull read rash may appear all over the body, especially on the trunk. Mortality ranges from 1 to 60%. Death either occurs as a direct result of the disease, or from secondary effects, such as bacterial pneumonia, encephalitis, or circulatory failure. If death occurs, it is usually by the end of the second week of infection. Despite these tragic statistics, many people around the world do not understand or believe how deadly scrub typhus can be until it is too late. Unfortunately, too many people are unwittingly dancing with death.

FIELD OF THE INVENTION

This invention relates to detecting exposure to and identification of microorganisms by the use of serodiagnostic assays, and more specifically to detecting exposure to and identification toward a truncated protein of at least one strain of *Orientia tsutsugamushi* based on its strength in reactivity. Additionally, this invention related to the production of vaccines, passive prophylactic or therapeutic agents and detection or identification reagents. The products produced in accordance with this invention may be combined with other pharmaceutically-acceptable bioactive substances.

DESCRIPTION OF PRIOR ART

Scrub typhus is caused by *O. tsutsugamushi*, a gram negative bacterium. In contrast to other gram negative bacteria, *O. tsutsugamushi* has neither lipopoly-saccharide nor a peptidoglycan layer (1) and the ultrastructure of its cell wall differs significantly from those of its closest relatives, the typhus and spotted fever group species in the genus *Rickettsia* (33). The major surface protein antigen of *O. tsutsugamushi* is the variable 56 kDa protein which accounts for 10-15% of its total protein (16, 28). Most type-specific monoclonal antibodies to *Orientia* react with homologues of the 56 kDa protein (16, 24, 42). Sera from most patients with scrub typhus recognize this protein, suggesting that it is a good candidate for use as a diagnostic antigen (28).

Diagnosis of scrub typhus is generally based on the clinical presentation and the history of a patient. However, differentiating scrub typhus from other acute tropical febrile illnesses such as leptospirosis, murine typhus, malaria, dengue fever, and viral hemorrhagic fevers can be difficult because of the similarities in signs and symptoms. Highly sensitive polymerase chain reaction (PCR) methods have made it possible to detect *O. tsutsugamushi* at the onset of illness when antibody titers are not high enough to be detected (14, 19, 36). PCR amplification of the 56 kDa protein gene has been demonstrated to be a reliable diagnostic method for scrub typhus (14, 18). Furthermore, different genotypes associated with different *Orientia* serotypes could be identified by analysis of variable regions of this gene without isolation of the organism (14, 17, 18, 25, 39). However, gene amplification requires sophisticated instrumentation and reagents generally not available in most rural medical facilities. Current serodiagnostic assays such as the indirect immunoperoxidase (IIP) test and the indirect immunofluorescent antibody (IFA) or microimmunofluorescent antibody (MIF) tests require the propagation of *rickettsiae* in infected yolk sacs of embryonated chicken eggs or antibiotic free cell cultures (4, 20, 30, 43).

At the present time the only commercially available dot-blot immunologic assay kits (Dip-S-Ticks) requires tissue culture grown, Renografin density gradient purified, whole cell antigen (41). Only a few specialized laboratories have the ability to culture and purify *O. tsutsugamushi* since this requires biosafety level 3 (BL3) facilities and practices. The availability of recombinant *rickettsial* protein antigens which can be produced and purified in large amounts and have similar sensitivity and specificity to *rickettsia*-derived antigens would greatly reduce the cost, transport, and reproducibility problems presently associated with diagnostic tests which require the growth and purification of *rickettsiae*. Furthermore, large-scale growth and purification of the scrub typhus *rickettsiae* are prohibitively expensive.

Recently, a recombinant 56 kDa protein from Boryong strain fused with maltose binding protein was shown to be suitable for diagnosis of scrub typhus in a enzyme-linked immunosorbent assay (ELISA) and passive hemagglutination test (21, 22). Although this protein overcomes some of the above-described disadvantages, it still has certain inherent disadvantages as an assay reagent because it is a fusion protein.

SUMMARY OF THE INVENTION

Accordingly, an object of this invention is a recombinant DNA construct and expressed polypeptide possessing immunogenic regions for the Karp, Kato and Gilliam strains of *O. tsutsugamushi.*

Another object of the invention, as described herein, is a recombinant polypeptide encoding a portion of the 56 kDa protein of *O. tsutsugamushi* encoded by amino acids 80 to 456 for Karp strain SEQ ID NO.: 1, 81-453 for Kato strain SEQ ID No. 4 and 81-448 for Gilliam strain SEQ ID NO.: 5.

A still further object of the invention is a recombinant truncated 56 kDa polypeptide which is re-folded to give a soluble moiety.

An additional object of this invention is the use of at least one recombinant polypeptide in antibody based assays for improved methods for the detection of *O. tsustugamushi* exposure and/or identification of at least one of its Karp, Kato or Gilliam strains in research and in clinical samples.

Yet another object of the invention is the expression of truncated r56 polypeptides in different host backgrounds of bacterial strains for use in different vaccine formulations against scrub typhus infection.

These and other objects, features and advantages of the present invention are described in or are apparent from the following detailed description of preferred embodiments.

BRIEF DESCRIPTION OF THE DRAWINGS

The invention will be further described with reference to the drawings, in which like elements have been denoted throughout by like reference numerals. The representation in each of the figures is diagrammatic and no attempt is made to indicate actual scales or precise ratios. Proportional relationships are shown as approximations.

FIG. 1 shows the strategy for cloning and construction of pWM1 that expresses the truncated recombinant 56 kDa protein antigen from *O. tsutsugamushi* Karp strain.

FIG. 2 shows the HPLC ion exchange profile for the purification of r56. The insert shows the Coomassie blue staining (A) and Western blot analysis (B) of the two peak fractions at 25 (left lane) and 27 min (right lane) which contain most of the r56.

FIG. 3 shows the circular dichroism spectrum of refolded r56.

FIG. 4 shows a comparison of ELISA IgG reactivity of r56 and *O. tsutsugamushi* Karp strain whole cell lysate with rabbit antisera (see Table 1).

FIG. 5 shows a scattergram of IgG ELISA reactivity of 128 Thai patient sera obtained with folded r56 and the corresponding IIP test IgG titers.

FIG. 6 shows a scattergram of IgM ELISA reactivity of 128 Thai patient sera obtained with folded r56 and the corresponding IIP test IgM titers.

FIG. 7 shows the time course of IgM and IgG reactivity of confirmed cases of scrub typhus by ELISA with folded r56 as antigen.

DETAILED DESCRIPTION

There is a critical need for rapid assays for the determination of exposure to *Orientia tsutsugamushi*, the causative agent of scrub typhus. Currently available assays require bacterial antigen which must be purified by extremely labor intensive methods after first propagating the organism in specialized laboratories (BSL-3). Furthermore, there is currently no efficacious vaccine for scrub typhus.

Recombinantly produced protein antigens of *O. tsutsugamushi* and recognized by specific antibodies would greatly facilitate the practical use of anti-scrub typhus assays since the protein can be produced more economically. Additionally, recombinant polypeptides can be used in sub-unit vaccines.

In accordance with the practice of this invention, a recombinant, refolded non-fusion polypeptide expressed from a truncated r56 gene of the causative agent of scrub typhus, *Orienta tsutsugamushi* for the Karp, Kato and Gilliam strains has been produced. The invention is useful for detecting prior exposure to scrub typhus, screening for and/or identification of at least one infectious strain-similarity (i.e. a Karp-like, Kato-like, or Gilliam-like strain) based on its strength of reaction toward a truncated protein and as a component in vaccine formulations and production of immune globulins for passive prophylaxis and immunity in subjects.

The 56 kDa protein of *O. tsutsugamushi* is extremely abundant in the bacteria and is highly immunogenic. Although the use of recombinant 56 kDa protein from *O. tsutsugamushi* has been reported, it was produced as a fusion peptide which creates a number of inherent disadvantages, including reduced immunogenicity due to improper folding of the bacteria polypeptide. To overcome these problems a non-fusion, recombinant polypeptide from 56 kDa protein was produced using the following alternative procedures designated herein as PROCEDURES I and II to express and purify r56 from the Karp, Kato and/or Gilliam strains. Furthermore, as illustrated herein for the production of SEQ ID No. 1, in order to ensure proper folding of the polypeptide after translation, and therefore enhanced immune recognition, a truncated recombinant 56 kDa gene was created with the truncation created at specific points (Seq ID No. 1). The truncated 56 kDa gene is then expressed using efficient expression systems. This truncated, recombinant polypeptide is then use as antigen in antibody based assays and to induce an immune response against scrub typhus. The specification generally uses the Karp strain for illustrative purposes only, as the following examples apply to other strains of O. tsutsugamushi, including the Kato and Gilliam strains.

EXAMPLE 1

Cloning and Expression of Recombinant 56 kDa Gene.

As shown in FIG. 1, a primer pair (56F(226/261), 5'-TTG-GCTGCA<u>CATATG</u>ACAATCGCTCCAGGAT TTAGA-3' (Seq. ID No. 2) and 56R(1409/1363), 5'-CTTTCTAGAAG-TATAAGCTAACCC<u>GGATCC</u> AACACCAGCCTATAT-*TGA*-3' (Seq. ID No. 3) was designed using the nucleotide sequence of the open reading frame for the Karp 56 kDa protein (34). The respective restriction sites for Nde I and BamH I are underlined and the new initiation codon and reverse complement of the new stop codon are shown in bold and italic, respectively. The forward primer 56F(226/261) contained the methionine initiation codon, at residue 80, which is part of the Nde I recognition sequence. The reverse primer 56R(1409/1363) created an alteration of the tyrosine codon at residue 457 to a stop codon and contained a BamH I site. The coding sequence from amino acid 80 to 456 was amplified by polymerase chain reaction (PCR), using the above primers, from DNA isolated from plaque-purified O. tsutsugamushi Karp strain grown in irradiated L929 cells (18). The truncated 56 kDa gene was amplified in a mixture of 400 mM each of deoxynucleotide triphosphate, 1 mM of each primer, 1.5 U of Taq polymerase (Perkin-Elmer, CA) in 10 mM Tris-HCl buffer, pH 8.3, 1.5 mM $MgCl_2$, and 50 mM KCl. The PCR reaction was started with 15 sec at 80° C., 4 min at 94° C., and followed by 30 cycles of 94° C. for 1 min, 57° C. for 2 min and 72° C. for 2 min. The last cycle was extended for 7 min at 72° C. The amplified fragment (1.18 kb) was digested with Nde I (BioLab, MA) and BamH I (Life Technology, MD) and ligated with doubly digested expression vector. Any plasmid or viral expression system can be used as long as polypeptide is expressed. The preferred expression system is the plasmid system pET11a (Novagen, WI) (FIG. 1) to yield the expression system pWM1. The E. coli strain HB101 was transformed with the ligation mixture and colonies screened for inserts with the right size and orientation.

Expressed r56 is constructed such that the N-terminal 79 residues or the C-terminal 77 residues of the intact 56 kDa protein, as deduced from the open reading frame of its encoding gene, is not present. Both regions deleted were predicted to be relatively hydrophobic and be responsible for association with the rickettsial outer membrane. Truncation of these termini facilitate the refolding of the expressed polypeptide and favors its solubility in aqueous solutions and simplification of handling.

Purification of the 56 kDa Protein.

Figure 2:
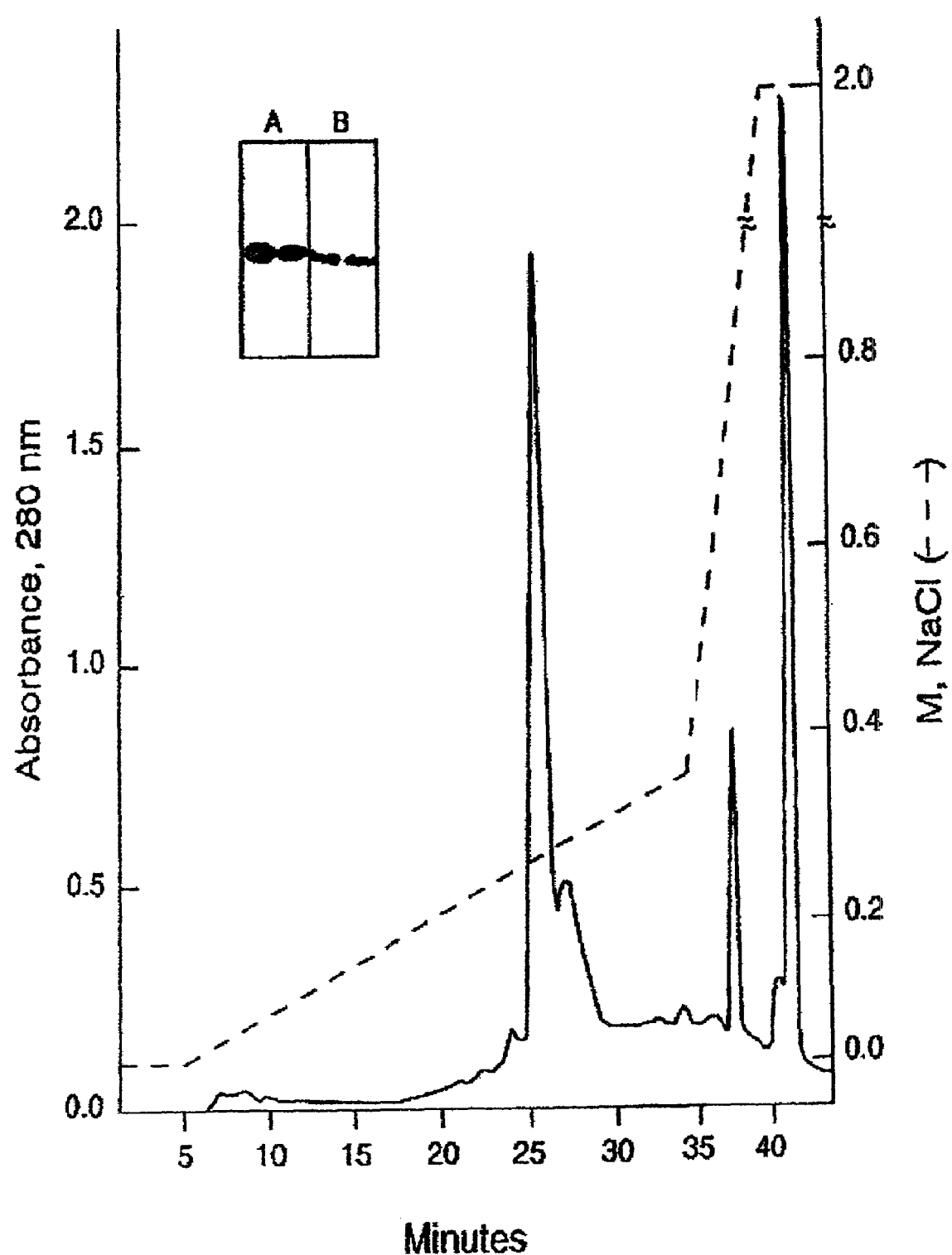

Plasmids carrying the insert of the truncated and amplified 56 kDa gene are transformed into the expression host E. coli BL21. The optimum time and IPTG concentration for r56 expression is determined. Recombinant E. coli expressing r56 are grown overnight at 37° C. with shaking. Cell pellets from 100 ml cultures are resuspended in 3 ml of buffer A (20 mM Tris-HCl, pH 8.0), containing 5 mM EDTA and 1 mM PMSF. Ultrasonic disruption of the cell is performed with cooling on ice. Disrupted cell extract is centrifuged at 8,000×g for 30 min. The pellets are vortexed to a homogeneous suspension with 2 M urea in buffer A, placed on a shaker at room temperature for an additional 10 min, centrifuged for 5 min at 14,000 rpm in an Eppendorf centrifuge (model 5415). The entire process is then repeated with 4 M urea in buffer A. Finally the pellets are dissolved in 8 M urea in buffer A and applied onto an HPLC ion exchange (DEAE) column (Waters, 0.75 cm×7.5 cm) for fractionation. Proteins are eluted with a linear gradient of buffer B and buffer C (6 M urea and 2 M NaCl in buffer A) from 0.0 to 0.4 M NaCl over 30 min at a flow rate of 0.5 ml/min. Fractions are collected, typically at one min per fraction. For a typical run, approximately 200 µl of extract obtained from a total of 10 ml culture is loaded onto the column (FIG. 2). The presence of r56 in fractions was detected by dot-blot immunoassay. Positive fractions with significant amounts of protein, presumably containing expressions of the truncated and amplified 56 kDa gene, are also analyzed by SDS-PAGE and Western blotting.

Testing for Polypeptide Expression by Dot-Blot Immunoassay.

Fractions collected from HPLC are screened for r56 polypeptide by dot-blot assay. A 2 µl sample of each eluted fraction is diluted into 200 µl of water and applied to a well of a 96-well dotblotter (Schleicher and Schuell). After drying under vacuum for 5 min, the nitrocellulose membrane is blocked with 5% nonfat milk for 30 min, then incubated with monoclonal antibody Kp56c specific for Karp 56 kDa protein antigen (23) for one hr, washed 4 times with phosphate buffer saline (PBS) 5 min each time, and incubated with peroxidase conjugated goat anti-mouse IgG (H+L) (Bio-Rad Laboratories) for 30 min. After washing with PBS 5 times for 5 min, substrate solution containing 5:5:1 ratio of TMB peroxidase substrate, hydrogen peroxide solution, and TMB membrane enhancer (Kirkegaard and Perry Laboratories) is added onto the nitrocellulose membrane. The enzymatic reaction is stopped after 2 min by washing the membrane in distilled water. The above-described test can be incorporated into any dot-blot, spot or dipstick type test structure. These structures are extensively described in the prior art.

Confirmation of Polypeptide Identity.

Confirmation of the identity of the polypeptide is confirmed by amino acid sequence analysis of SDS-PAGE purified, CNBr cleaved fragments of the peak fractions (7). The sequences are identical to that deduced from nucleotide.

Refolding of r56.

HPLC fractions, in 6M urea, containing peak r56 polypeptide are pooled and sequentially dialyzed against 4 M urea and 2 M urea in buffer A and finally with buffer A only. The final dialysis is against buffer A with two initial changes of buffer for 30 min each, and finally overnight at 4° C. r56 is properly folded since the polypeptide remains soluble in buffer A with no urea present.

Circular Dichroism (CD) Spectrum of r56.

The circular dichroism spectrum of refolded r56 was measured on a JASCO model 715 in Dr. Ettore Apella=s laboratory in NIH, Bethesda, Md. Data were analyzed by Dr. Latchezar I. Tsonev, Henry Jackson Foundation, Rockville, Md., at a protein concentration of 117 µg/ml in 20 mM Tris HCl, pH 8.0 and the calculated molecular weight of 40,903 dalton.

Figure 3:
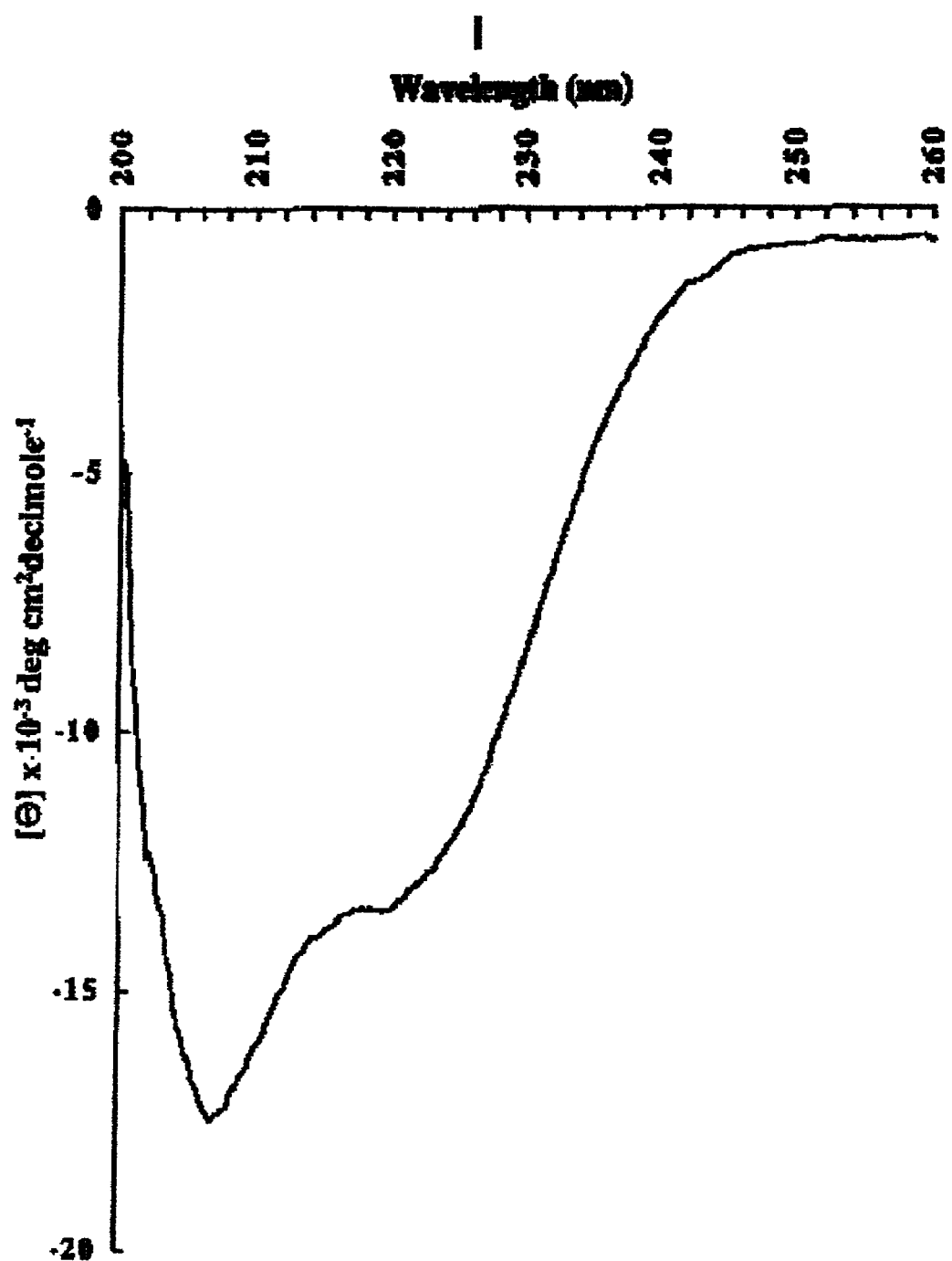

The CD spectrum of the refolded polypeptide shows that the secondary structure is approximately 38% α-helical, 13% β-sheet and 50% random coil (15) (FIG. 3). This experimental data is similar to that predicted by correctly folded, truncated 56 kDa protein, based on amino acid sequence from nucleic acid sequence (34).

EXAMPLE 2

Use of r56 Polypeptide in Antibody Based Identification Assays.

ELISA Assay Method

The microtiter plates are coated with antigens diluted in PBS overnight at 4° C. and blocked with 0.5% boiled casein for 1 hr, rinsed with PBS twice, 5 min each time. Patient sera are diluted 1:400 with 20 µg/ml of control protein extracts purified from *E. coli* BL21 using a procedure identical to that used for purifying r56 (fractions 21-32 pooled from gradients equivalent to FIG. 2), pre-absorbed for about 1 hr at room temperature, and then added to the ELISA plates. The plates are incubated for 1 hr at room temperature, washed four times with 0.1% Triton X-100 in PBS. Peroxidase conjugated mouse anti-human IgG (Fc specific) (Accurate) diluted 1:8000 and goat anti human IgM (µ chain specific) (Kirkegaard & Perry) are then added. After 1 hr incubation at room temperature, the plates are washed four times with 0.1% Triton X-100 in PBS and the last wash is with PBS only before the addition of substrate ABTS (Kirkegaard & Perry). The ODs at 405 nm are read after 15 min incubation at room temperature. Rabbit sera were diluted 1:250 with PBS only. All procedures are the same as for detection of human antibodies except that rabbit sera is not preabsorbed with protein preparations from BL21 and peroxidase conjugated goat anti-rabbit IgG (Kirkegaard & Perry) diluted 1:2,000 is used.

Figure 4:
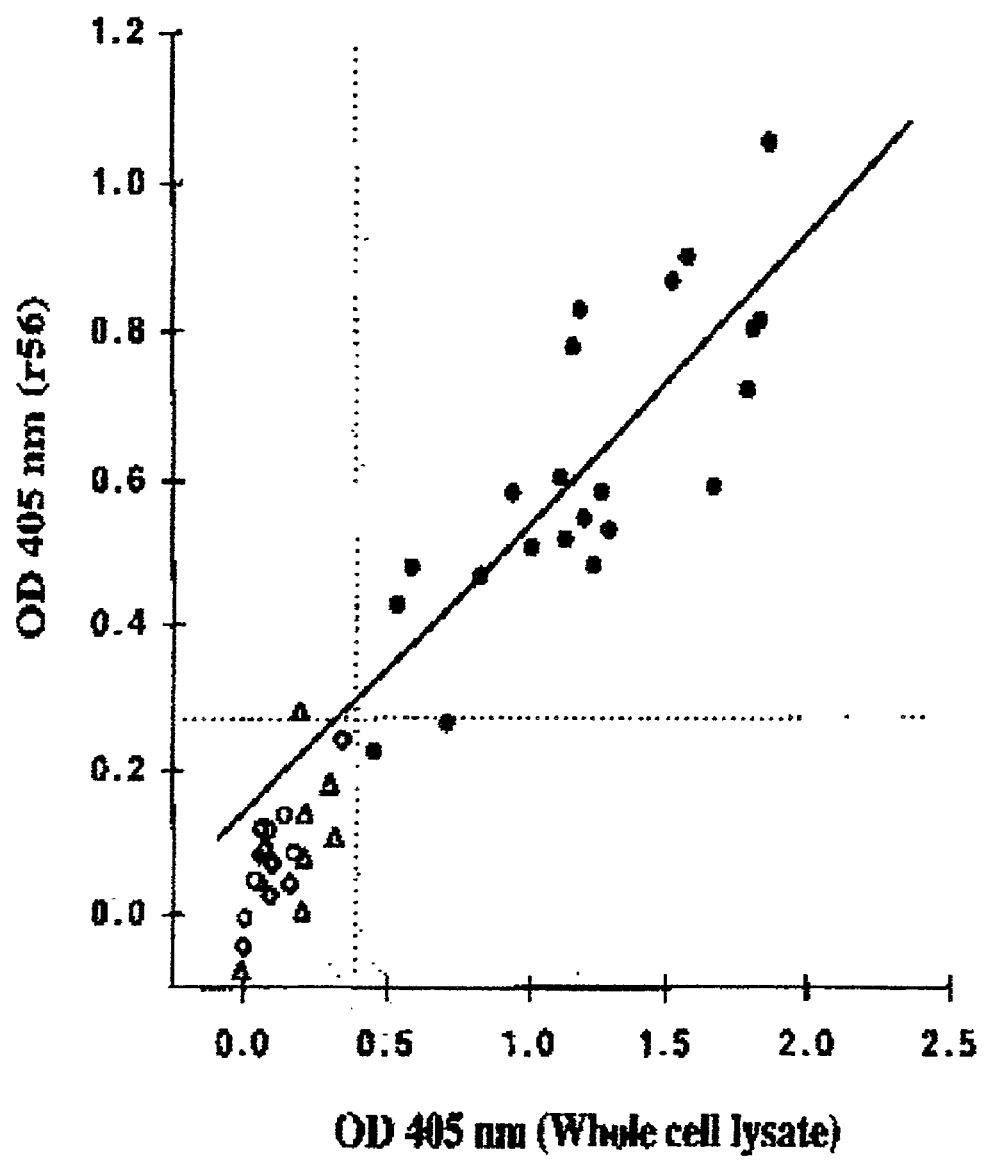

The recombinant r56 polypeptide contains only a portion of the 56 kDa protein, the major antigen that is used to differentiate antigenic types of *Orientia*. In addition rickettsial whole cell lysate contains numerous other protein antigens besides intact 56 kDa antigen. A comparison of ELISA IgG reactivity of r56 and *O. tsutsugamushi* Karp strain whole cell lysate with rabbit antisera is shown (FIG. 4). The dotted lines represent the mean+2 standard deviations of reactivity of the normal rabbit sera. The solid line is the linear regression of the data for the 22 anti-*Orientia* rabbit sera tested (r=0.81). Eight control normal rabbit sera (open diamonds); five antisera against non-*rickettsial* antigens (open triangles): eight antisera to *Rickettsiales* other than *Orientia* (open squares); and 22 antisera to eight antigen prototypes of *O. tsutsugamushi* (solid circles) are compared. Positive breakpoints (mean+2SD) for reactivity of both r56 and whole cell *Orientia* lysate (WCEX) and standard ELISA using eight normal rabbit (ODs of 0.27 and 0.38), respectively, are established. (FIG. 4, Table 1). None of the eight rabbits immunized with other species of *Rickettsiales* or the five antisera prepared against either L-cell, yolk sac, or *E. coli* exhibit reactivity higher than the cutoff for WCEX while one rabbit antiserum against primary chick embryo reacted barely above the breakpoint with r56 (OD of 0.28) (FIG. 4, Table 1). On the other hand 20 of 22 rabbit antisera against the eight *Orientia* antigenic prototypes react slightly above the breakpoint with r56 and all sera exhibit positive ELISA with WCex (FIG. 4, Table 1). Although the r56 antigen exhibits lower ELISA reactivity at the amount employed than that obtained with WCex, the *Orientia* rabbit antisera exhibit a very good correlation of ELISA reactions to the two antigens (r=0.8, n=22). One Kato antiserum and one TA686 antiserum which exhibit relatively low positive ELISA reactivity with WCex does not react, significantly, with r56 antigen (Table 1). Consequently, the ELISA with folded r56 gives equivalent results as the standard ELISA in the detection of *Orientia*-specific antibodies by ELISA (specificity-92.3%, sensitivity-90.9%, accuracy-91.4%) with WCEx ELISA as the reference assay) even though r56 is only a truncated portion of one of the complex antigens found in WCex.

TABLE 1

Comparison of ELISA reactivity of purified Karp whole cell lysate and folded r56 with rabbit antisera.

| Antisera against different antigens | ELISA ODs(405 nm) of whole cell lysate (corresponding r56 result) |
|---|---|
| *O. tsutsugamushi* strain | |
| Karp | 0.94 (0.58), 1.87 (1.04), 1.81 (0.80), 1.83 (0.81) |
| Kato | 0.46 (0.22), 1.02 (0.50), 1.16 (0.77), 1.27 (0.58) |
| Gilliam | 0.54 (0.42), 1.20 (0.54) |
| TH1817 | 1.67 (0.59), 1.12 (0.60), 1.29 (0.53), 0.83 (0.47) |
| TA678 | 0.59 (0.48) |
| TA686 | 0.71 (0.26), 1.52 (0.86) |
| TA716 | 1.24 (0.48), 1.14 (0.51) |
| TA763 | 1.79 (0.72), 1.57 (0.89), 1.18 (0.82) |
| Other Rickettsiales | |
| *R. prowazekii* | 0.08 (0.12) |
| *R. typhi* | 0.18 (0.08) |
| *R. rickettsii* | 0.06 (0.04), 0.15 (0.14) |
| *R. conorii* | 0.10 (0.11), 0.07 (0.11) |
| *E. sennetsu* | 0.01 (0.05) |
| *E. risticii* | 0.01 (−0.01) |
| Non rickettsial antigens | |
| Yolk sac | 0.22 (0.08) |
| L929-cell | 0.01 (−0.08) |
| Primary chick embryo | 0.20 (0.28) |
| RAW 264.7 cells | 0.22 (0.14) |
| *E. coli* HB101 | 0.32 (0.11) |
| No antigen control (n = 8) | 0.135 + 0.123 (0.093 + 0.088) |

[a]OD values listed are the difference between data with antigen and without antigen.

Comparison of r56 ELISA with IIP Test with Human Sera.

Figure 5:
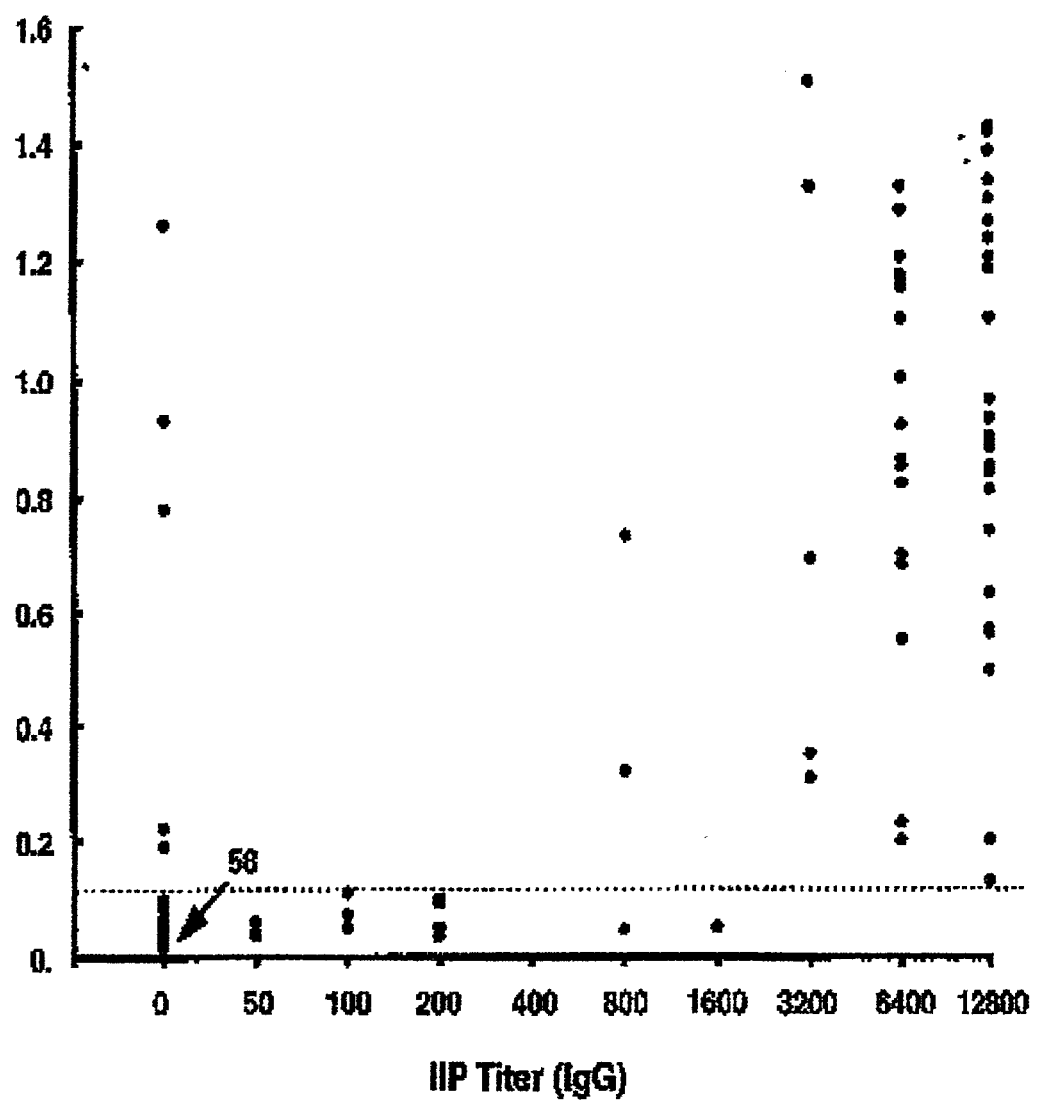
Figure 6:
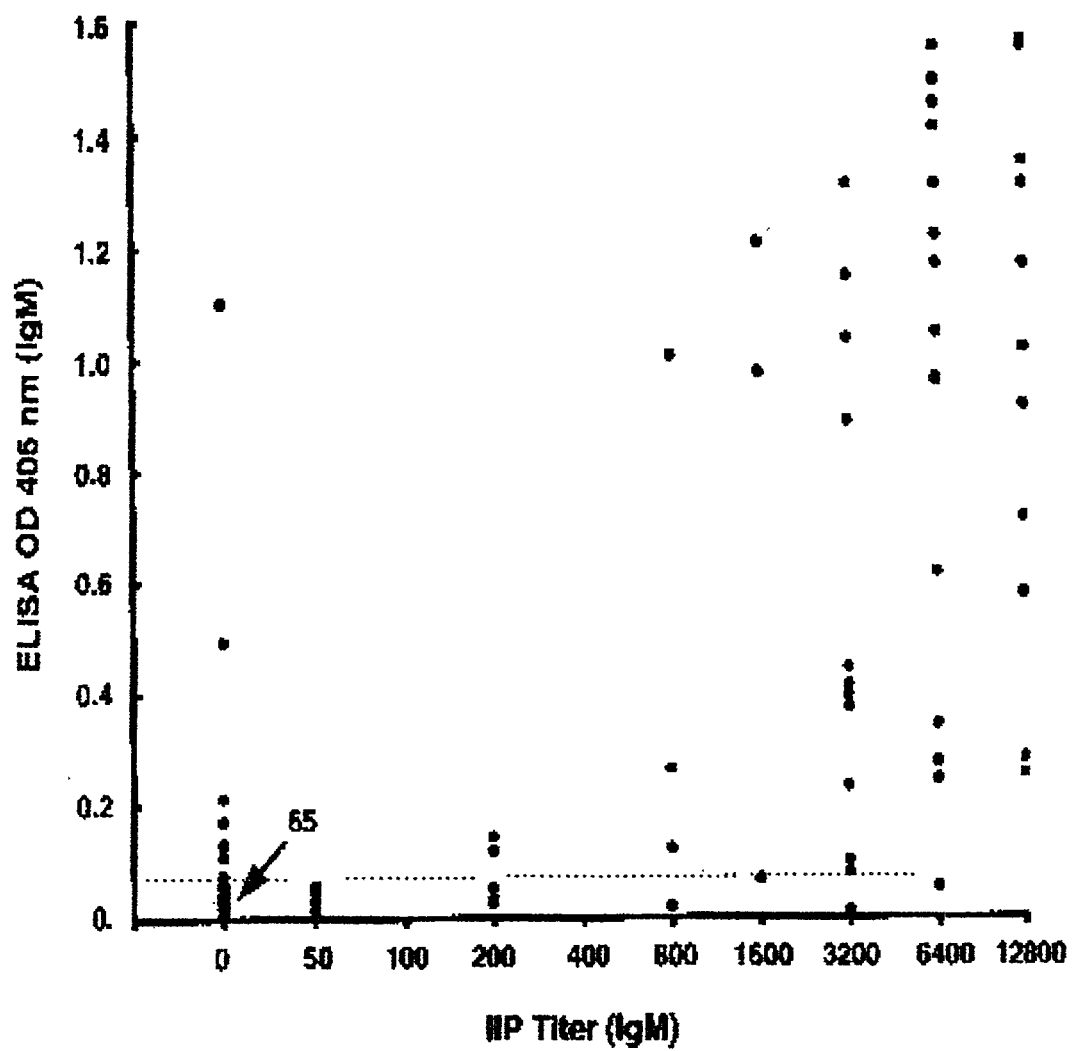

Seventy-four sera from healthy Thai soldiers were used to establish an ELISA break point for positive reactions (mean+2 SD) with r56 as antigen. These are 0.05+0.06=0.11 OD for IgG, and 0.032+0.032=0.064 OD for IgM at 1:400 serum dilution. The r56 ELISA ODs of 128 sera from patients suspected of scrub typhus from Korat, Thailand were compared with the IgG and IgM titers determined by an IIP method using a mixture of intact Karp, Kato, and Gilliam prototypes of *Orientia*. The IIP method used was described previously (20, 38) (FIGS. 5 and 6). Using IIP titers as the gold standard, the sensitivity, specificity, and accuracy values of ELISA results with the 128 test sera are calculated using different positive breakpoints for the IIP test (Table 2).

TABLE 2

Comparison of efficiency of r56 ELISA with the indirect immunoperoxidase assay (IIP) for 128 Thai patient sera.

| Titer | Ig | No. pos. sera by IIP | ELISA % Sensitivity | % Specificity | % Accuracy |
|---|---|---|---|---|---|
| 1:50 | IgG | 68 | 82% | 92% | 87% |
|  | IgM | 56 | 91% | 92% | 91% |
| 1:200 | IgG | 61 | 92% | 93% | 92% |
|  | IgM | 52 | 98% | 92% | 95% |
| 1:400 | IgG | 57 | 90% | 93% | 95% |
|  | IgM | 47 | 100% | 93% | 93% |

Figure 7:
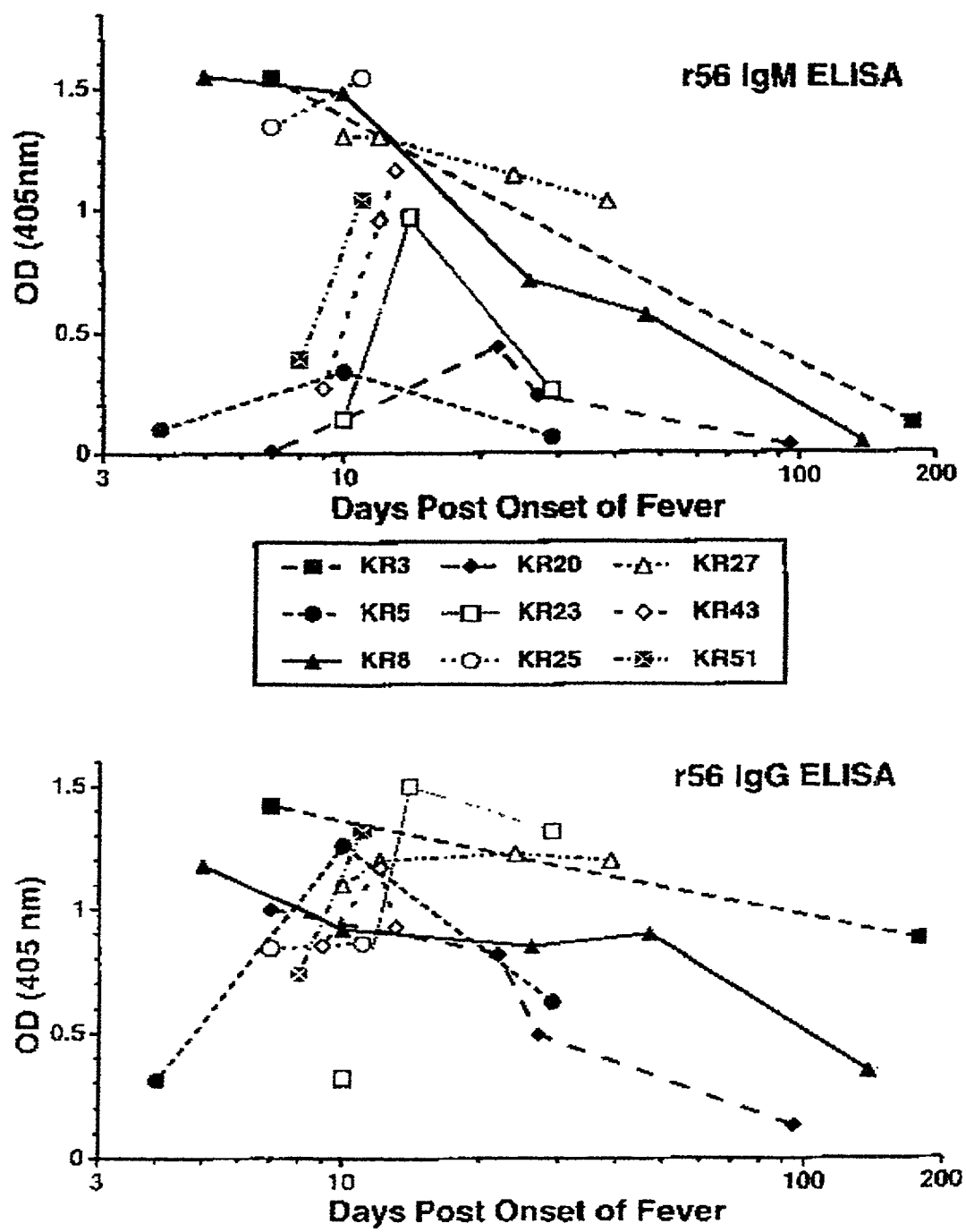

Sera from 13 isolate and PCR-confirmed cases of scrub typhus were analyzed to characterize the kinetics and magnitude of the IgM and IgG immune responses as measured by IIP test titers and by r56 ELISA ODs. Representative data are shown in FIG. 7 and Table 3. Four sera from 4 different cases were available from the first week after onset of fever (days 4-7). All are positive by IIP for both IgM and IgG with titers between 3200 and 12,800 for all cases. In contrast, by ELISA, KR5 (day 4, Table 3) has very low IgM and IgG ODs and KR20 is negative for IgM even at day 7 while the other two sera (KR8, KR25) are more reactive by IgM assay than IgG. Sixteen sera from 12 cases were collected 8-14 days post onset of fever. By IIP both IgM and IgG titers are again high and within one two-fold dilution for all of these sera except the day 10 serum from KR23 which also has the lowest IgM and IgG ELISA OD's (Table 3, FIG. 7). Except for three other sera from days 8-10 (KR5, KR43, KR51) which also had low IgM ODs, most sera has similar IgG and IgM ELISA reactions. Five sera from four cases were obtained in weeks 3-4 after infection. Two of the cases (KR8, KR20) exhibit a decrease in IgM ODs by ELISA at this time point which are not apparent by IIP assay while the other reactions all remain strong. In weeks 5-6 after infection two of 5 sera from different patients decline in IIP IgM titers (but not IgG titers) while three sera decline significantly in ELISA IgM and one by ELISA IgG. In striking contrast, KR27 maintain high levels of specific antibody as measured by all assays from 10 to 39 days (Table 3). With all six sera collected from six different cases 95-202 days post onset of illness, IgM IIP titers and both IgM and IgG ELISA ODs drop significantly; in contrast, only one of the sera exhibit a decline in IgG IIP titers (FIG. 7).

TABLE 3

Comparison of IIP test titers with ELISA r56 OD's obtained with human sera from confirmed cases of scrub typhus.

| Patient | Days post Onset of fever | IIP Test Titer IgM | IgG | r56 ELISA (OD) IgM | IgG |
|---|---|---|---|---|---|
| KR5 | 4 | 3,200 | 3,200 | 0.10 | 0.31 |
| KR5 | 10 | 6,400 | 12,800 | 0.34 | 1.26 |
| KR5 | 29 | 1,600 | 12,800 | 0.07 | 0.63 |
| KR8 | 5 | 12,800 | 12,800 | 1.55 | 1.18 |
| KR8 | 10 | 6,400 | 6,400 | 1.48 | 0.92 |
| KR8 | 26 | 12,800 | 12,800 | 0.71 | 0.85 |
| KR8 | 47 | 12,800 | 12,800 | 0.57 | 0.90 |
| KR8 | 137 | 50 | 3,200 | 0.05 | 0.35 |
| KR10 | 10 | 12,800 | 6,400 | 1.30 | 1.15 |
| KR10 | 201 | 200 | 6,400 | 0.053 | 0.20 |
| KR20 | 7 | 3,200 | 6,400 | 0.01 | 1.00 |
| KR20 | 22 | 3,200 | 6,400 | 0.44 | 0.82 |
| KR20 | 27 | 6,400 | 12,800 | 0.24 | 0.50 |
| KR20 | 95 | 200 | 6,400 | 0.03 | 0.13 |
| KR23 | 10 | 200 | 800 | 0.14 | 0.32 |
| KR23 | 14 | 1,600 | 3,200 | 0.97 | 1.50 |
| KR23 | 29 | 800 | 3,200 | 0.26 | 1.32 |
| KR25 | 7 | 12,800 | 12,800 | 1.34 | 0.84 |
| KR25 | 11 | 6,400 | 6,400 | 1.54 | 0.86 |
| KR27 | 10 | 3,200 | 6,400 | 1.30 | 1.10 |
| KR27 | 12 | 6,400 | 12,800 | 1.30 | 1.20 |
| KR27 | 24 | 3,200 | 12,800 | 1.14 | 1.23 |
| KR27 | 39 | 3,200 | 12,800 | 1.03 | 1.20 |
| KR43 | 9 | 6,400 | 6,400 | 0.27 | 0.85 |
| KR43 | 12 | 6,400 | 6,400 | 0.96 | 1.17 |
| KR43 | 13 | 12,800 | 12,800 | 1.16 | 0.93 |
| KR51 | 8 | 3,200 | 12,800 | 0.39 | 0.74 |
| KR51 | 11 | 6,400 | 6,400 | 1.04 | 1.32 |

The excellent sensitivity and specificity of the r56 ELISA in comparison with those of the IIP assay suggest that one protein antigen, i.e. truncated r56, is sufficient for detecting anti-*Orientia* antibody in sera from patients with scrub typhus. Use of a single moiety in recombinant form improves efficiency of the assay and will reduce cost per assay, significantly.

EXAMPLE 4

Induction of Protective Immune Response.

Because of the significant antibody response exhibited after exposure with *O. tsutsugamushi* in rabbits and humans, and the excellent recognition pattern of r56 polypeptide compared to whole cell extracts, the r56 polypeptide is a good candidate vaccine component.

Two strains of either relatively outbred mice (CD1) or an inbred strain (C3H) were immunized, with adjuvant with the r56 polypeptide. At various times after administration of the polypeptide the animals were challenged with live *O. tsutsugamushi.*

The protective efficacy of administration of r56 polypeptide is shown in table 4.

TABLE 4

Protection of Mice by Immunization with r56

| Experiment | Strain of mice | Dose/Mouse (adjuvant) | Challenge date post immunization | % Protection |
|---|---|---|---|---|
| I | C3H | 25 μg (incomp. Freunds) | 3 weeks | 100% |
| II | CD1 | 25 μg (Titer Max) | 4 months | 60% |
| III | CD1 | 2 μg (Titer Max) | 4 weeks | 60% |

Karp, Kato and Gilliam Strains

The variable 56 kDa major outer membrane protein of *Orientia tsutsugamushi* is the immunodominant antigen in human scrub typhus infections. The gene encoding this protein from Gilliam strain and Katostrain was cloned into the expression vector pET24a. The recombinant protein (r56) was expressed as a truncated non-fusion protein (amino acid 81 to amino acid 488 of the open reading frame for Gilliam and amino acid 81 to amino acid 453 of the open reading frame for Kato strain). Both protein formed an inclusion body when expressed in *Escherichia coli* BL21. The refolded r56 (Gilliam) and r56(Kato) were reactive to sera from scrub typhus patient. Three recombinant antigens, r56(karp), r56 (Gilliam), and r56(Kato) were mixed at an equal ratio and used as the antigen in an ELISA. A panel of patient sera exhibiting a wide range of reactivity was employed to compare the reactivity of mixed recombinant r56 antigens with mixed whole cell antigens. The ELISA results correlated well to those obtained using whole cell lysate from the corresponding strains as the coating antigen in the ELISA. These results strongly support that the mixture of the recombinant proteins has the potential to be used as a diagnostic reagent, exhibiting broad sensitivity and high specificity for scrub typhus infection and in production of immune globulins, vaccines, and therapeutic agents. The recombinant r56(Gilliam) and r56(Kato) have the potential to replace the density gradient-purified, *rickettsia*-derived, whole cell antigen currently used in the commercial dipstick assay available in the USA.

The molecular cloning, expression, purification, and refolding of the truncated non-fusion 56 kDa protein from Gilliam strain, r56(Gilliam), and from Kato strain, r56(Kato) will now be described. The refolded r56(Gilliam) reacted strongly with monoclonal antibody (mAb) RK-G3C51 but did not react with mAb E+95. The r56 (Kato) reacted with E+95, but not with RK-G3C51. The strain variations of *Orientia* are well documented. In order to develop a diagnostic reagent that will detect most cases of scrub typhus infection, different serotype antigens need to be included in the antigen cocktail employed. A mixture of three purified recombinant r56 (Karp, Gilliam and Kato) was evaluated for its reactivity with 20 patient sera which exhibited wide range of reactivity with whole cell lysate cocktail of strains Karp, Gilliam, and Kato in a standard ELISA for diagnosis of scrub typhus. The ELISA results of using mixture of r56 correlated well to those obtained using the mixture of corresponding strains of whole cell lysate. These results strongly suggest that the recombinant proteins have the potential to be used as diagnostic reagents, exhibiting broad sensitivity and high specificity for scrub typhus infection.

Bacterial Strains and Vectors. *Escherichia coli* HB101 was used for cloning and *E. coli* BL21(DE3) was used for overexpression of proteins under the control of phage T7lac promoter (26). The plasmid vector used was pET-24a (Novagen, Madison, Wis.). Plaque-purified *O. tsutsugamushi* Gilliam and Kato strains were grown in irradiated L929 cells was used for preparation of the genomic DNA (11).

Cloning of the gene for the r56 (Gilliam) into the expression vector pET24a. A primer pair 56FGm(784/819), 5' T T A G C T G C G C.dwnarw.A T A T G A C A A T T G C A C C A G G A T T T A G A 3' (SEQ ID NO. 6) and r56RGm (1929/1894) 5' A T G A G C T A A C C C G.dwnarw.G A T C C A A C A C C A G C C T A T A T T G A 3' (SEQ ID NO. 7) was designed using the nucleotide sequence of the open reading frame for the Gilliam 56 kDa protein (27). The respective restriction sites for Nde I and BamH I are underlined and bold. The forward primer 56FGm(784/819) contained the methionine initiation codon, at residue 81, which is part of the Nde I recognition sequence. The reverse primer 56RGm(11929/1894), mutated the tyrosine codon at residue 448 to a stop codon and contained a BamH I site. The coding sequence from amino acid 81 to 448 was amplified by PCR from DNA isolated from *O. tsutsugamushi* Gilliam strain. Cloning of the gene for the r56 (Kato) into the expression vector pET24a. A primer pair 56FKt (785/820), 5' T T A G C T G C A C.dwnarw.A T A T G A C A A T C G C G C C A G G A T T T A G A 3' SEQ ID NO. 8 and r56RKt (1945/1910), 5' A T A A G C T A A C C C G.dwnarw.G A T C C A A G A C C A G C C T A T A T T G A 3' (SEQ ID NO. 9 was designed using the nucleotide sequence of the open reading frame for the Kato 56 kDa protein (31). The respective restriction sites for Nde I and BamH I are underlined and bold. The forward primer 56FGm(784/819) contained the methionine initiation codon, at residue 81, which is part of the Nde I recognition sequence. The reverse primer 56RGm (11929/1894), mutated the tyrosine codon at residue 448 to a stop codon and contained a BamH I site. The coding sequence from amino acid 81 to 448 was amplified by PCR from DNA isolated from *O. tsutsugamushi* Gilliam strain.

Cloning of the gene for the r56 (Kato) into the expression vector pET24a. A primer pair 56FKt(785/820), 5' <u>TTA GCT GCA C</u>↓<u>ATATG</u> ACA ATC GCG CCA GGA TTT AGA 3' and r56RKt (1945/1910), 5' ATA AGC TAA CCC G↓GA TCC AAG ACC AGC CTA TAT TGA 3' was designed using the nucleotide sequence of the open reading frame for the Kato 56 kDa protein (31). The respective restriction sites for Nde I and BamH I are underlined and bold. The forward primer 56FGm(784/819) contained the methionine initiation codon, at residue 81, which is part of the Nde I recognition sequence. The reverse primer 56RGm (11929/1894), mutated the tyrosine codon at residue 448 to a stop codon and contained a BamH I site. The coding sequence from amino acid 81 to 448 was amplified by PCR from DNA isolated from *O. tsutsugamushi* Gilliam strain.

The two truncated 56 kDa genes were amplified in a mixture of 400 mM each of deoxynucleotide triphosphate, 1 mM of each primer, 1.5 U of Taq polymerase (Perkin-Elmer-Cetus, Norwalk, Conn.) in 10 mM Tris-HCl buffer, pH 8.3, 1.5 mM $MgCl_2$, and 50 mM KCl. The PCR reaction was started with 15 sec at 80° C., 4 min at 94° C., and followed by 30 cycles of 94° C. for 1 min, 57° C. for 2 min and 72° C. for 2 min. The last cycle was extended for 7 min at 72° C. The amplified fragments was digested with Nde I (New England BioLabs, Beverly, Mass.) and BamH I (GIBCO-BRL Life Technology, Gaithersburg, Md.) and ligated with doubly digested expression vector pET24a. *E. coli* HB101 was transformed with the ligation mixture and colonies screened for inserts with the right size and orientation.

Procedure I

Expression and purification of the r56 (Gilliam) and r56(Kato). Plasmids carrying the insert were transformed into the expression host *E. coli* BL21. The optimum time and isopropyl-□-D-thiogalactopyranoside (IPTG) concentration for inducing r56 expression was determined. Recombinant *E. coli* expressing r56 (Gilliam) were propagated overnight in 2X YT (16 g bacto-tryptone, 10 g bacto-yeast extract, and 5 g NaCl per liter of distilled water, pH 7.0) at 37° C. with shaking. Cell pellets from 100 ml cultures were resuspended in 3 ml of buffer A (20 mM Tris-HCl, pH 8.0), containing 5 mM EDTA. Ultrasonic disruption of the cell was performed using setting 3 on a Sonicator Ultrasonic Liquid Processor Model XL2020 with standard tapered microtip (Heat Systems, Inc., Farmingdale, N.Y.), six times for 20 sec with cooling on ice for 1 min between each sonication. Disrupted cell extract was centrifuged at 8,000×g for 30 min. The pellets were vortexed to a homogeneous suspension with 2 M urea in buffer A, placed on a shaker at room temperature for an additional 10 min, centrifuged for 5 min at 14,000 rpm in an Eppendorf centrifuge (model 5415). The entire process was then repeated with 2% sodium deoxycholate in buffer A. Finally the pellets were dissolved in 8 M urea in buffer A. The supernant was applied onto an high pressure liquid chromatography (HPLC) ion exchange (DEAE 5PW) column (Waters Associates, Milford, Mass.) (0.75 cm×7.5 cm) for fractionation. Proteins were eluted with a linear gradient of buffer B (6 M urea in buffer A) and buffer C (6 M urea and 2 M NaCl in buffer A) from 0.0 to 0.4 M NaCl over 30 min at a flow rate of 0.5 ml/min. Fractions were collected at one min per fraction. The presence of r56 in fractions was detected by dot blot immunoassay. Positive fractions with significant amounts of protein were analyzed by SDS-PAGE and Western blotting.

Dot blot immunoassay. A 2 μl sample of each eluted fraction was diluted into 200 μl of water and applied to a well of a 96-well dotblotter (Schleicher and Schuell, Keene, N.H.). After drying under vacuum for 5 min, the nitrocellulose membrane was blocked with 5% nonfat milk for 30 min, then incubated with antibody specific for Gilliam or Kato 56 kDa protein antigen for 1 hr, washed 4 times with phosphate buffer saline (PBS) 5 min each time, and incubated with peroxidase conjugated goat anti-mouse IgG (H+L) (Bio-Rad Laboratories, Richmond, Calif.) for 30 min. After washing with PBS 5 times for 5 min, substrate solution containing 5:5:1 ratio of TMB (tetramethylbenzidine) peroxidase substrate, hydrogen peroxide solution, and TMB membrane enhancer (Kirkegaard and Perry Laboratories, Gaithersburg, Md.) was added onto the nitrocellulose membrane. The enzymatic reaction was stopped after 2 min by washing the membrane in distilled water.

SDS-PAGE and Western Blot analysis. Sodium dodecyl sulfate-polyacrylamide gel electrophoresis (SDS-PAGE) analysis was performed with the mini-protein II Dual Slab Cell System (8.2 cm×7.2 cm×0.75 cm, Bio-Rad). The stacking gel and separation gel contained 4% and 10% acrylamide (acrylamide:bisacrylamide ratio was 30:1), respectively. Electrophoresis was carried out at constant voltage of 125 V for 75 min. The gels were either stained with Coomassie Blue R or electroblotted onto nitrocellulose membrane. Immunodetection of the Western blot was the same as described for the dot blot immunoassay.

Refolding of r56. Refolding of r56(Gilliam) and r56 (Kato) in 6 M urea in buffer A were achieved by sequential dialysis with 4 M urea and 2 M urea in buffer A and finally with buffer A only. The peak fractions from the DEAE column were combined and dialyzed against 8 volumes of 4 M urea in buffer A for 30 min at room temperature followed with one change of the dialysis solution and dialyzed for an additional 30 min. The same procedure was repeated with 2 M urea in buffer A. The final dialysis was against buffer A with two initial changes of buffer for 30 min each, and finally overnight at 4° C.

Human sera. Patient sera were collected from Pescadore Islands in 1976 (2).

ELISA. 96 well microtiter plates were coated overnight at 4° C. with antigens diluted in PBS and blocked with 0.5% boiled casein for 1 hr, rinsed with PBS twice, 5 min each time. Linbro U plates (Cat. No. U 76-311-05, ICN, Costa Mesa, Calif.) were used for assays with rabbit sera while Microtest III tissue culture plates (Falcon #3072) were employed with human sera. Patient sera were diluted 1:100 in PBS. The plates were incubated for 1 hr at room temperature, washed four times with 0.1% Triton X-100 in PBS. Peroxidase conjugated mouse anti-human IgG (Fc specific) (Accurate Chemical and Scientific Corp., Westbury, N.Y.) diluted 1:2000. After 1 hr incubation at room temperature, the plates were washed four times with 0.1% Triton X-100 in PBS and the last wash was with PBS only before the addition of substrate ABTS (Kirkegaard & Perry). Optical densities (ODs) at 405 nm were measured at 10 min and 15 min at room temperature.

Table 5 lists the ELISA data of 20 patient sera. The ELISA results using the mixture of three recombinant r56 polypeptides correlated well to those obtained using whole cell lysate from the corresponding strains as the coating antigen. A basic problem in the design of diagnostic tests for *Orientia* is that numerous serotypes exist. Eight prototypes (Gilliam, Karp, Kato, TA686, TA716, TA678, TA763, TH1817) have been widely used as reference strains for MIF serotyping of isolates collected throughout the areas endemic for *Orientia* (7, 24). In recent years several additional serotypes from Japan and Korea have been recognized (5, 22, 33). We have recently characterized more than 200 *Orientia* isolates by restriction fragment length polymorphism (RFLP) analysis of four different antigen gene homologues following their amplification by polymerase chain reaction (6, 11). 45 RFLP variant types were identified. The dominant human immune response is against the variable 56 kDa outer membrane protein which is the major antigen distinguished in serotyping. Some of the antigenic serotypes found in Japan and Taiwan have recently been further subdivided by RFLP analysis of their 56 kDa genes (10, 18, 29). Both specific and cross-reactive domains exist in different homologues of this protein. DNA sequence analysis of 56 kDa genes from various serotypes has revealed that the sequences may be divided into four conserved and four variable domains (19). These conserved domains of 56 kDa protein may account for the cross-reactivity of antisera against diverse serotypes while the variable domains are very likely responsible for some of the serotype specificity observed in *Orientia*. The r56 recombinant proteins lack most of the conserved regions of the 56 kDa protein at both the N- and C-terminus. The conserved regions between the first and the second variable domain and between the second and the third variable domain are relatively short. Consequently, the broad reactivity of r56 may be due to the conserved region located between the third and the fourth variable domain which is about 160 residue long. The four variable domains are responsible for the strain specificity in serological tests. The *O. tsutsugamushi* strains Karp, Gilliam, and Kato have been shown to be antigenically distinct. They were isolated from different geographic areas (Karp from New Guinea, Gilliam from Burma, Kato from Japan). Recently a rapid flow assay for diagnosis of scrub typhus using r56 (Karp) (36, 37) was developed. To improve upon the broad reactivity of this RFA, r56 antigens were produced from strains Gilliam and Kato to be included in the RFA for future evaluation at clinical sites.

In summary, the 56 kDa major variable outer membrane protein antigen of *O. tsutsugamushi* is the immunodominant antigen in human infections. Further, the strain variations of *Orientia* are well documented. In order to develop a diagnostic reagent that will detect most cases of scrub typhus infection, the preferred embodiment of the invention includes the r56 Karp antigen alone, when prepared by PROCEDURE II or in combination with or b. most preferably, a combination of different serotype antigens in the antigen cocktail employed.

The gene encoding this protein from the Karp strain (amino acid 80-456, designated as r56) was cloned, expressed, and purified in accordance with PROCEDURE I. In following PROCEDURE I relative to the Kato and Gilliam strains, the 56 kDa protein from the Kato strain and the Gilliam strain were expressed with slight modifications to the procedure (PROCEDURE I) that was used to express and purify r56 from the Karp strain. This modification is attributable to the use of different primer in the production of each of the r56 Karp (SEQ ID NO.1), r56 Kato (SEQ ID NO.4), and r56 Gilliam (SEQ ID NO.5) polypeptides. The r56 Gilliam and r56 Kato are truncated at both the N and C-termini, and exhibited the expected size by SDS-PAGE (amino acids 81-448 for r56 Gilliam, total of 368 amino acids; amino acids 81-453 for r56 Kato, total of 373 amino acid). The r56 Gilliam did not react with monoclonal antibody E+95 but reacted strongly with RK-G3C51. The r56 Kato reacted with E+95, but not with RK-G3C51. These three r56 antigens were mixed at an equal ratio and used as the antigen in an ELISA. A panel of patient sera exhibiting a wide range of reactivity was employed to compare the reactivity of mixed recombinant r56 antigens with mixed whole cell antigens. The ELISA results correlated well to those obtained using whole cell lysate from the corresponding strains as the coating antigen in the ELISA. These results provide strong scientific evidence which supports that the mixture of the recombinant proteins has the potential to be used as a diagnostic reagent, exhibiting broad sensitivity and high specificity for scrub typhus infection.

Similarly, inventor had further developed as a further embodiment of this invention, an improved method (PROCEDURE II) for the production of Karp r56, Kato r56 and Gilliam r56. Surprisingly, the final products prepared in accordance with this new method were produced in substantially higher concentration and purity and with less impurities and less aggregates as compared to the products prepared by the previous process (PROCEDURE I) disclosed herein. More specifically, the improved method (PROCEDURE II) is as follows:

Procedure II

1. Expression of r56: Plasmids carrying the insert were transformed into the expression host *E. coli* BL21. Recombinant *E. coli* expressing r56 were induced with isopropyl-beta-D-thiogalactopyranoside (IPTG) in the log phase and propagated in LB medium over night at 37° C. with shaking.

2. Purification of r56 polypeptide: The r56 polypeptides were expressed as inclusion bodies (IB) in *E. coli* BL21. Cell pellets were re-suspended in buffer A (20 mM Tris-HCl, pH 8.0), containing 5 mM EDTA and 0.1 mM of phenylmethylsulfonyl fluoride (PMSF). The cells were disrupted by passing through microfluidizer three times and the cell extract was centrifuged at 8,000×g for 30 min. The pellets were extracted with 2 M urea in buffer A and dissolved in 8 M urea containing 10-20 mMDTT for 2.5 to 5 mg/ml of r56. After incubation at room temperature for at least 20 minutes, the sample solution was centrifuged at 8,000×g for 5 minutes. The clear supernatant (<1/10 of the column volume) was applied to size-exclusion columns TSK P3000SW (21.5 mm×50 cm) -tandem TSK P4000SW (21.5 mm×100 cm) column equilibrated with 8 M urea and 1 mM DTT in 20 mM Tris-HCl, pH 7.8 (buffer B). Peak fractions containing the r 56 polypeptide were pooled and loaded into the anion-exchange DEAE column (21.5 mm×30 cm). The bound r56 was eluted with a linear gradient of NaCl from 0 to 0.4 M in buffer B over 30-60 min at a flow rate of 5 ml/min.

3. Refolding of the purified r56 polypeptide: Refolding of r56 in buffer B were achieved by sequential dialysis with 6 M urea, 4 M urea, and 2 M urea in buffer A and finally with buffer A only. The peak fractions from the DEAE column were combined and dialyzed against 8 volumes of 6 M urea in buffer A for 30 minutes at 4 degrees Celsius (4 C) followed with two changes of the dialysis solution and dialyzed for a total of an additional 60 minutes. The same procedure was repeated with 4 M and 2 M urea in buffer A, except 0.3 uM of oxidized form of glutathione was included in the 4M urea solution. The final dialysis was against buffer A with two initial changes of buffer for 30 min each, and finally overnight at 4 C.

Protection Efficacy data for (a) r56 (Karp only), (b) r56 (Kato only) and (c) a mixture of r56 Karp, r56 Kato and r56 Gilliam, challenged by Kato.

TABLE 5

Immunoprotection of Swiss Outbred CD1 Mice from Orientia tsutsugamushi Karp Strain with Kp r56 Vaccine using Freund's Incomplete Adjuvant and Alum + CpG.

| VACCINE | ADJUVANT | BOOST | PROTECTION | SEROLOGY |
|---------|----------|-------|------------|----------|
| PBS | FIA | — | 38.5% | 0.10 ± 0.25 |
| PBS | FIA | Boost | 52.9% | 0.06 ± 0.06 |
| PBS | Alum-CpG | — | 41.2% | 0.12 ± 0.09 |
| PBS | Alum-CpG | Boost | 30.8% | 0.06 ± 0.07 |
| Kp r56 | FIA | — | 100% | 1.56 ± 0.15 |
| Kp r56 | FIA | Boost | 95% | 1.49 ± 0.37 |
| Kp r56 | Alum-CpG | — | 76.9% | 1.48 ± 0.08 |
| Kp r56 | Alum-CpG | Boost | 73.7% | 1.42 ± 0.12 |

FIA = Freund's Incomplete Adjuvant

FIA=Freund's Incomplete Adjuvant

IP Challenge of Swiss Outbred CD1 Mice

TABLE 6

Dose Dependence of Immunoprotection of Swiss Outbred CD1 Mice from Orientia tsutsugamushi Kato Strain with Kato r56 Vaccine in the presence of Freund's Incomplete Adjuvant.

| Vaccine (Kato r56) | Protection |
|--------------------|------------|
| 0.0 ug | 0% |
| 0.8 ug | 14% |
| 2.5 ug | 43% |
| 8.0 ug | 43% |
| 25 ug | 57% |

IP challenge of Swiss Outbred CDl Mice

TABLE 7

Efficacy of the trivalent vaccine (KpKtGm r56) against homologous challenge of Kato strain.

| Challenge Strain of *O. tsutsugamushi* | Vaccinated Mice (#survived/total#) | Unvaccinated Mice (#survived/total#) |
|---|---|---|
| PBS | 7/7 | 7/7 |
| Kato(1,000 LD50;IP) | 4/7* | 0/7 |

*Time to death was increased slightly by vaccination when compared to unvaccinated (PBS injected) control mice.

IP challenge of Swiss outbred CDl mice.

The inventors have disclosed efficacy data which supports the use of one, two or all three antigens in a monovalent, bivalent and trivalent pharmaceutical composition, immunogenic composition and vaccine, respectively. One of ordinary skill in the art will readily recognize that DNA only approach, a protein only approach, or a prime-boost approach using DNA in the initial dose and protein in the following dose may be used for the vaccine.

It is contemplated by the inventor(s) that the following five (5) categories of bioactive substances, combinations thereof and their use are within the scope of this invention:

1. r56 Karp prepared by PROCEDURE I and II
2. r56 Karp prepared by PROCEDURE I and II in combination with r56 Kato prepared by PROCEDURE I and II
3. r56 Karp prepared by PROCEDURE I and II in combination with r56 Gilliam prepared by PROCEDURE I and II
4. rKarp prepared by PROCEDURE I and II,
   rKato prepared by PROCEDURE I and II,
   rGilliam prepared by PROCEDURE I and II, and
5. Each of the categories (1-4)herein above in combination with other bioactive and pharmaceutically-acceptable.

REFERENCES

1. Amano, K., A. Tamura, N. Ohashi, H. Urakami, S. Kaya, and K. Fukushi. 1987. Deficiency of peptidoglycan and lipopolysaccharide components in *Rickettsia tsutsugamushi*. Infect. Immun. 55:2290-2292.
2. Blanar, M. A., D. Kneller, A. J. Clark, A. E. Karu, F. E. Cohen, R. Langridge, and I. D. Kuntz. 1984. A model for the core structure of the *Escherichia coli* RecA protein. Cold Spring Harb. Symp. Quant. Biol. 49:507-511.
3. Bourgeois, A. L., J. G. Olson, R. C. Fang, J. Huang, C. L. Wang, L. Chow, D. Bechthold, D. T. Dennis, J. C. Coolbaugh, and E. Weiss. 1982. Humoral and cellular responses in scrub typhus patients reflecting primary infection and reinfection with *Rickettsia tsutsugamushi*. Am. J. Trop. Med. Hyg. 31:532-540.
4. Bozeman, F. M., and B. L. Elisberg. 1963. Serological diagnosis of scrub typhus by indirect immunofluorescence. Proc. Soc. Exp. Biol. Med. 112:568-573.
5. Brown, G. W., D. M. Robinson, D. L. Huxsoll, T. S. Ng, K. J. Lim, and G. Sannasey. 1976. Scrub typhus: a common cause of illness in indigenous populations. Trans. R. Soc. Trop. Med. Hyg. 70: 444-448.
6. Brown, G. W., J. P. Saunders, S. Singh, D. L. Huxsoll, and A. Shirai. 1978. Single dose doxycycline therapy for scrub typhus. Trans. R. Soc. Trop. Med. Hyg. 72:412-416.
7. Chang W-H. 1995. Current status of *tsutsugamushi* disease in Korea. J. Korean Med. Sci. 10:227-238.
8. Ching, W.-M., H. Wang, and G. A. Dasch. 1996. Identification of human antibody epitopes on the 47 kDa, 56 kDa, and 22 kDa protein antigens of *Orientia tsutsugamushi* with synthetic peptides. Amer. J. Trop. Med. Hyg. 55:300. Abstract # 608
9. Cohen, F. E., R. M. Abarbanel, I. D. Kuntz, and R. J. Fletterick. 1983. Secondary structure assignment for $\alpha/\beta$ proteins by a combinatorial approach. Biochemistry 22:4894-4904.
10. Crum, J. W., S. Hanchalay, and C. Eamsila. 1980. New paper enzyme-linked immunosorbent technique compared with microimmunofluorescence for detection of human serum antibodies to *Rickettsia tsutsugamushi*. J. Clin. Microbiol. 11:584-588.
11. Dasch G. A., S. Halle, and L. Bourgeois. 1979. Sensitive microplate enzyme-linked immunosorbent assay for detection of antibodies against the scrub typhus *rickettsia,*
12. Dasch. G. A., D. Strickman, G. Watt, and C. Eamsila. 1996. Measuring genetic variability in *Orientia tsutsugamushi* by PCR/RFLP analysis: a new approach to questions about its epidemiology, evolution, and ecology, p. 79-84. In J. Kazar (ed.) *Rickettsiae* and *Rickettsial* Diseases. Vth International Symposium. Slovak Academy of Sciences, Bratislava.
13. Dohany A. L., A. Shirai, D. M. Robinson, S. Ram, and D. L. Huxsoll. 1978. Identification and antigenic typing of *Rickettsia tsutsugamushi* in naturally infected chiggers (Acarina: Trombiculidae) by direct immunofluorescence. Am. J. Trop. Med. Hyg. 27:1261-1264.
14. Furuya, Y., Y. Yoshida, T. Katayama, F. Kawamori, S. Yamamoto, N. Ohashi, A. Kamura, and A. Kawamura, Jr. 1991. Specific amplification of *Rickettsia tsutsugamushi* DNA from clinical specimen by polymerase chain reaction. J. Clin Microbiol. 29: 2628-2630.
15. Greenfield, N., and G. D. Fasman. 1969. Computed circular dichroism spectra for the evaluation of protein conformation. Biochemistry 10:4108-4116.
16. Hanson, B. 1985. Identification and partial characterization of *Rickettsia tsutsugamushi* major protein immunogens. Infect. Immun. 50:603-609.
17. Horinouchi, H., K. Murai, A. Okayama, Y. Nagatomo, N. Tachibana, and H. Tsubouchi. 1996. Genotypic idenfication of *Rickettsia tsutsugamushi* by restriction fragment length polymorphism analysis of DNA amplified by the polymerase chain reaction. Am. J. Trop. Med. Hyg. 54:647-651.
18. Kelly, D. J., G. A. Dasch, T. C. Chye, and T. M. Ho. 1994. Detection and characterization of *Rickettsia tsutsugamushi* (*Rickettsiales: Rickettsiaceae*) in infected *Leptotrombidium* (*Leptotrombidium*) *fletcheri* chiggers (Acari: Trombiculidae) with the polymerase chain reaction. J. Med. Entomol. 31:691-699.
19. Kelly, D. J., D. Marana, C. Stover, E. Oaks, and M. Carl. Detection of *Rickettsia tsutsugamushi* by gene amplification using polymerase chain reaction techniques. Ann. N.Y. Acad. Sci. 590:564-571.
20. Kelly, D. J., P. W. Wong, E. Gan, and G. E. Lewis, Jr. 1988. Comparative evaluation of the indirect immunoperoxidase test for the serodiagnosis of *rickettsial* disease. Am. J. Trop. Med. Hyg. 38:400-406.
21. Kim, I-S., S-Y. Seong, S-G. Woo, M-S. Choi, and W-H. Chang. 1993. High-level expression of a 56-kilodalton protein gene (bor56) of *Rickettsia tsutsugamushi* Boryong and its application to enzyme-linked immunosorbent assays. J. Clin. Microbiol. 31:598-605.

22. Kim, I-S., S-Y. Seong, S-G. Woo, M-S. Choi, and W-H. Chang. 1993. Rapid diagnosis of scrub typhus by a passive hemagglutination assay using recombinant 56-kilodalton polypeptide. J. Clin. Microbiol. 31:2057-2060.
23. Moree, M. F., and B. Hanson. 1992. Growth characteristics and proteins of plaque-purified strains of *Rickettsia tsutsugamushi*. Infect. Immun. 60:3405-3415.
24. Murata, M. Y. Yoshida, M. Osono, N. Ohashi, Oyanagi, H. Urakami, A. Tamura, S. Nogami, H. Tanaka, and A. Kawamura, Jr. 1986. Production and characterization of monoclonal strain-specific antibodies against prototype strains of *Rickettsia tsutsugamushi*. Microbiol. Immunol. 30:599-610.
25. Ohashi, N., Y. Koyama, H. Urakami, M. Fukuhara, A. Tamura, F. Kawamori, S. Yamamoto, S. Kasuya, and K. Yoshimura. 1996. Demonstration of antigenic and genotypic variation in *Orientia tsutsugamushi* which were isolated in Japan, and their classification into type and subtype. Microbiol. Immunol. 40:627-638.
26. Ohashi, N., H. Nashimoto, H. Ikeda, and A. Tamura. 1992. Diversity of immunodominant 56-kDa type-specific antigen (TSA) of *Rickettsia tsutsugamushi*. Sequence and comparative analyses of the genes encoding TSA homologues from four antigenic variants. J. Biol. Chem. 267:12728-12735.
27. Ohashi, N., A. Tamura, M. Ohta, and K. Hayashi. 1989. Purification and partial characterization of a type-specific antigen of *Rickettsia tsutsugamushi*. Infect. Immun. 57:1427-1431.
28. Ohashi, N., A. Tamura, H. Sakurai, and T. Suto. 1988. Immunoblotting analysis of anti-*rickettsial* antibodies produced in patients of tsutsugamushi disease. Microbiol. Immunol. 32:1085-1092.
29. Ohashi, N., A. Tamura, H. Sakurai, and S. Yamamoto. 1990. Characterization of a new antigenic type, Kuroki, of *Rickettsia tsutsugamushi* isolated from a patient in Japan. J. Clin. Microbiol. 28:2111-2113.
30. Robinson, D. M., G. Brown, E. Gan, and D. L. Huxsoll. 1976. Adaptation of a microimmunofluorescence test to the study of human *Rickettsia tsutsugamushi* antibody. Am. J. Trop. Med. Hyg. 25:900-905.
31. Saunders, J. P., G. W. Brown, A. Shirai, and D. L. Huxsoll. 1980. The longevity of antibody to *Rickettsia tsutsugamushi* in patients with confirmed scrub typhus. Trans. Roy. Soc. Trop. Med. Hyg. 74:253-257.
32. Shirai, A., D. M. Robinson, G. W. Brown, E. Gan, and D. L. Huxsoll. 1979. Antigenic analysis by direct immunofluorescence of 114 isolates of *Rickettsia tsutsugamushi* recovered from febrile patients in rural Malaysia. Japan J Med Sci Biol 32:337-344.
33. Silverman, D. J., and C. L. Wisseman, Jr. 1978. Comparative ultrastructural study on the cell envelopes of *Rickettsia prowazekii, Rickettsia rickettsii*, and *Rickettsia tsutsugamushi*. Infect. Immun. 21(3):1020-1023.
34. Stover, C. K., D. P. Marana, J. M. Carter, B. A. Roe, E. Mardis, and E. V. Oaks. 1990. The 56-kilodalton major protein antigen of *Rickettsia tsutsugamushi*: molecular cloning and sequence analysis of the sta56 gene and precise identification of a strain-specific epitope. Infect. Immun. 58(7):2076-2084.
35. Studier, F. W., and B. A. Moffatt. 1986. Use of bacteriophage T7 RNA polymerase to direct selective high-level expression of cloned genes. J. Mol. Biol. 189:113-130.
36. Sugita, Y., T. Nagatani, K Okuda, Y. Yoshida, and H. Nakajima. 1992. Diagnosis of typhus infection with *Rickettsia tsutsugamushi* by polymerase chain reaction. J. Med. Microbiol. 37:357-360.
37. Suto, T. 1980. Rapid serological diagnosis of *tsutsugamushi* disease employing the immuno-peroxidase reaction with cell cultured *rickettsia*. Clin. Virol. 8:425
38. Suwanabun, N., C. Chouriyagune, C. Eamsila, P. Watcharapichat, G. A. Dasch, R. S. Howard, and D. J. Kelly. 1997. Evaluation of an enzyme-linked immunosorbent assay in Thai scrub typhus patients. Am. J. Trop. Med. Hyg. 56:38-43
39. Tamura, A., N. Ohashi, Y. Koyama, M. Fukuhara, F. Kawamori, M. Otsuru, P-F. Wu, and S-Y. Lin. 1997. Characterization of *Orientia tsutsugamushi* isolated in Taiwan by immunofluorescence and restriction fragment length polymorphism analyses. FEMS Microbiol. Lett. 150:225-231.
40. Urakami, H., S. Yamamoto, T. Tsuruhara, N. Ohashi, and A. Tamura. 1989. Serodiagnosis of scrub typhus with antigens immobilized on nitrocellulose sheet. J. Clin. Microbiol. 27:1841-1846.
41. Weddle, J. R., T. C. Chan, K. Thompson, H. Paxton, D. J. Kelly, G. Dasch, and D. Strickman. 1995. Effectiveness of a dot-blot immunoassay of anti-*Rickettsia tsutsugamushi* antibodies for serologic analysis of scrub typhus. Am. J. Trop. Med. Hyg. 53:43-46.
42. Yamamoto, S., N. Kawabata, A. Tamura, H. Urakami, N. Ohashi, M. Murata, Y. Yoshida, and A. Kawamura, Jr. 1986. Immunological properties of *Rickettsia tsutsugamushi*, Kawasaki strain, isolated from a patient in Kyushu. Microbiol. Immunol. 30:611-620.
43. Yamamoto, S., and Y. Minamishima. 1982. Serodiagnosis of *tsutsugamushi* fever (scrub typhus) by the indirect immunoperoxidase technique. J. Clin. Microbiol. 15:1128-1132.

Obviously, many modifications and variations of the present invention are possible in light of the above teachings. It is therefore to be understood that, within the scope of the appended claims, the invention may be practiced otherwise than as specifically described. It is contemplated that this invention can be used to develop and/or augment vaccine therapy, prophylactic and therapeutic treatments for other diseases caused by facultative intracellular pathogens and/or agents such as a virus, bacteria, fungus, venom, pollen, protozoal, and mixtures thereof.

Reference: Ohashi, N., H. Nashimoto, H. Ikeda, and A. Tamura 1990. Cloning and sequencing of the gene (tsg56) encoding a type-specific antigen from *Rickettsia tsutsugamushi*. Gene, 91, 119-122

The polypeptide from amino acid 81-448 of the intact protein SEQ ID NO.: 5 was cloned into PET24a expression vector. The total # of amino acids are 368.

```
>Gilliam sequence number 25 524 aa
MKKIMLIASA MSALSLPFSA SAIELGEEGG LECGPYGKVG

IVGGMITGAE STRLDSTDSE GKKHLSLTTG LPFGGTLAAG

MTIAPGFRAE LGVMYLRNIS AEVEVGKGKV DSKGEIKADS

GGGTDTPIRK RFKLTPPQPT IMPISIADRD VGVDTDILAQ

AAAGQPQLTV EQRAADRIAW LKNYAGIDYM VPDPQNPNAR

VINPVLLNIT QGPPNVQPRP RQNLDILDHG QWRHLVVGVT

ALSHANKPSV TPVKVLSDKI TKIYSDIKPF ADIAGIDVPD

TGLPNSASVE QIQSKMQELN DVLEDLRDSF DGYMGNAFAN
```

```
QIQLNFVMPQ QAQQQQGQGQ QQQAQATAQE AVAAAAVRLL

NGNDQIAQLY KDLVKLQRHA GVKKAMEKLA AQQEEDAKNQ

GEGDCKQQQG ASEKSKEGKG KETEFDLSMI VGQVKLYADL

FTTESFSIYA GVGAGLAHTY GKIDDKDIKG HTGMVASGAL

GVAINAAEGV YVDLEGSYMH SFSKIEEKYS INPLMASVGV

RYNF
```

Gilliam Strain

1. Primer 5GFGm (784/819) 36 bp Primer:
5' T T A G C T G C G C.dwnarw.A T A T G A
C A A T T G C A C C A G G A T T T A G A 3' Nde I
(SEQ ID NO. 6)

2. Primer 56RGm (1929/1894) 36 bp Primer:
5' A T G A G C T A A C C C G.dwnarw.G A
T C C A A C A C C A G C C T A T A T T G A 3' BamH I
(SEQ ID NO. 7)

Reference: Tamura, A., H. Ikeda, H. Nashimoto, and N. Ohashi. 1992. Diversity of immunodominant 56-kDa type-specific antigen(TSA) of *rickettsia tsutsugamushi*: Sequence and comparative analysis of the genes encoding TSA homologues from four antigenic variants. J. Biol. Chem. 267, 12728-12735

The polypeptide from amino acid 81-453 of the intact protein SEQ ID NO.: 4 was cloned into PET24a expression vector. The total # of amino acids are 373.

```
>Kato sequence number 21 529 aa
MKKTMLIASA MSALSLPFSA SAIELGDEGG LECGPYAKVG

VVGGMITGVE STRLDPADAG GKKQLPLTTS MPFGGTLAAG

MTIAPGFRAE LGVMYLANVK AEVESGKTGS DADIRSGADS

PMPQRYKLTP PQPTIMPISI ADRDLGVDIP NVPQGGANHL

GDNLGANDIR RADDRITWLK NYAGVDYMVP DPNNPQARIV

NPVLLNIPQG PPNANPRQAM QPCSILNEDH WRHLVVGITA

MSNANKPSVS PIKVLSEKIV QIYRDVKPFA RVAGIEVPSD

PLPNSASVEQ IQNKMQELND ILDEIRDSFD GCIGGNAFAN

QIQLNFRIPQ AQQQGQGQQQ QQAQATAQEA AAAAVRVLN

NNDQIIKLYK DLVKLKRHAG IKKAMEELAA QDGGCNGGGD

NKKKRGASED SDAGGASKGG KGKETKETEF DLSMIVGQVK

LYADLFTTES FSIYAGLGAG LAYTSGKIDG VDIKANTGMV

ASGALGVAIN AAEGVYVDTE GSYMHSFSKI EEKYSINPLM

ASFGVRYNF
```

Kato Strain

1. Primer 56FKt (785/820) 36 bp Primer:
5' T T A G C T G C A C.dwnarw.A T A T G A
C A A T C G C G C C A G G A T T T A G A 3' NdeI
(SEQ ID NO. 8)

2. Primer 56RKt (1945/1910) 36 bp Primer:
5'A T A A G C T A A C C C G G A T C C A A G
A C C A G C C T A T A T T G A 3'
(SEQ ID NO. 9)

Karp: Open Reading Frame (#556-#2151) and Cloned Sequence for Protein Expression (#793-#1923) (SEQ ID NO. 10)

```
 556 ATGAA AAAATTATG TTAATTGCTA GTGCAATGTC TGCGTTGTCG

601 TTGCCATTTT CAGCTAGTGC AATAGAATTG GGGGAAGAAG GATTAGAGTG TGGTCCTTAT

661 GCTAAAGTTG GAGTTGTTGG AGGAATGATT ACTGGCGTAG AATCTGCTCG CTTGGATCCA

721 GCTGATGCTG AAGGCAAAAA ACACTTGTCA TTAACAAATG GGCTGCCATT TGGTGGAACG

781 TTGGCTGCAG GTATGACAAT CGCTCCAGGA TTTAGAGCAG AGATAGGTGT TATGTACCTT

841 ACAAATATAA CTGCTCAGGT TGAAGAAGGT AAAGTTAAGG CAGATTCTGT AGGTGAGACA

901 AAGGCAGATT CTGTAGGTGG GAAAGATGCT CCTATACGTA AGCGGTTTAA ACTTACACCT

961 CCTCAGCCTA CTATAATGCC TATAAGTATA GCTGTACGTG ACTTTGGGAT TGATATTCCT

1021 AACCAGACCT CAGCAGCAAG CACAAGCCGC AGCCTCAGGC TTAATGATGA GCAACGTGCT

1081 GCAGCTAGGA TCGCTTGGTT AAAGAATTGT GCTGGTATTG ACTATAGGGT AAAAAACCCT

1141 AATGATCCTA ATGGGCCTAT GGTTATAAAT CCGATATTGT TAAATATTCC ACAGGGTAAC

1201 CCTAATCCTG TTGGAAATCC ACCGCAGCGA GCAAATCCGC CTGCAGGTTT TGCGATACAT

1261 AACCATGAGC AATGGAGGCA TTTGGTAGTT GGGCTTGCTG CATTATCAAA TGCTAATAAA
```

-continued

```
1321 CCTAGCGCTT CTCCTGTCAA AGTATTAAGT GATAAAATTA CTCAGATATA TAGTGATATA
1381 AAGCATTTGG CTGATATAGC TGGTATTGAT GTTCCTGATA CTAGTTTGCC TAATAGTGCA
1441 TCTGTCGAAC AGATACAGAA TAAAATGCAA GAATTAAACG ATCTATTGGA AGAGCTCAGA
1501 GAATCTTTTG ATGGGTATCT TGGTGGTAAT GCTTTTGCTA ATCAGATACA GTTGAATTTT
1561 GTCATGCCGC AGCAAGCACA GCAGCAGGGG CAAGGGCAGC AACAGCAAGC TCAAGCTACA
1621 GCGCAAGAAG CAGTAGCAGC AGCAGCTGTT AGGCTTTTAA ATGGCAATGA TCAGATTGCG
1681 CAGTTATATA AAGATCTTGT TAAATTGCAG CGTCATGCAG GAATTAAGAA AGCGATGGAA
1741 AAATTAGCTG CCCAACAAGA AGAAGATGCA AAGAATCAAG GTGAAGGTGA CTGCAAGCAG
1801 CAACAAGGAA CATCTGAAAA ATCTAAAAAA GGAAAAGACA AAGAGGCAGA GTTTGATCTG
1861 AGTATGATTG TCGGCCAAGT TAAACTCTAT GCTGACGTAA TGATAACTGA ATCAGTCTCA
1921 ATATATGCTG GTGTTGGTGC AGGGTTAGCT TATACTTCTG GAAAAATAGA TAATAAGGAT
1981 ATTAAAGGGC ATACAGGCAT GGTTGCATCA GGAGCACTTG GTGTAGCAAT TAATGCTGCT
2041 GAAGGTGTGT ATGTGGACAT AGAAGGTAGT TATATGTACT CATTCAGTAA AATAGAAGAG
2101 AAGTATTCAA TAAATCCTCT TATGGCAAGT GTAAGTGTAC GCTATAACTT C
```

The polypeptide from Amino Acid 80-456 of the intact protein SEQ ID NO.: 1) was cloned into PET 24a expression vector. The total number of Amino Acids are 377.

MTIAPGFRAEIGVMYLTNITAQVEEGKVKADSVGETKADSVGGKDAPIRK
RFKLTPPQPTIMPISIADRDFGIDIPNIPQQQAQAAQPQLNDEQRAAARI
AWLKNCAGIDYRVKNPNDPNGPMVINPILLNIPQGNPNPVGNPPQRANPP
AGFAIHNHEQWRHLVVGLAALSNANKPSASPVKVLSDKITQIYSDIKHLA
DIAGIDVPDTSLPNSASVEQIQNKMQELNDLLEELRESFDGYLGGNAFAN
QIQLNFVMPQQAQQQGQGQQQQAQATAQEAVAAAAVRLINGNDQIAQLYK
DLVKLQRHAGIKKAMEKLAAQQEEDAKNQGEGDCKQQQGTSEKSKKGKDK
EAEFDLSMIVGQVKLYADVMITESVSI

Kato: Open Reading Frame (#557-2143) (SEQ ID NO. 11) and Cloned Region for Protein Expression(#797-1915) is Bolded

```
 557 ATGA AAAAAATTAT GTTAATTGCT AGTGCAATGT CTGCATTGTC
 601 ATTGCCGTTT TCAGCTAGTG CGATAGAATT GGGGGATGAA GGAGGATTAG AGTGTGGTCC
 661 TTATGCTAAA GTTGGAGTCG TTGGAGGAAT GATTACTGGC GTAGAATCTA CTCGCTTGGA
 721 TCCAGCTGAT GCTGGTGGCA AAAAACAATT GCCATTAACA ACCTCGATGC CATTTGGTGG
 781 TACATTAGCT GCAGGTATGA CAATCGCGCC AGGATTTAGA GCAGAGCTAG GGGTTATGTA
 841 CCTTGCGAAT GTAAAAGCAG AGGTGGAATC AGGTAAAACT GGCTCTGATG CTGATATTAG
 901 ATCTGGTGCA GATTCTCCTA TGCCTCAGCG GTATAAACTT ACACCACCTC AGCCTACTAT
 961 AATGCCTATA AGTATTGCGG ATCGTGACCT TGGGGTTGAT ATTCCTAACG TACCTCAAGG
1021 AGGAGCTAAT CACCTGGGTG ATAACCTTGG TGCTAATGAT ATTCGGCGTG CTGACGATAG
1081 GATCACTTGG TTGAAGAATT ATGCTGGTGT TGACTATATG GTTCCAGATC CTAATAATCC
1141 TCAGGTAGA ATTGTAAATC CAGTGCTATT AAATATTCCT CAAGGTCCGC CTAATGCAAA
1201 TCCTAGACAA GCTATGCAAC CTTGTAGTAT ACTTAACCAT GATCACTGGA GGCATCTTGT
1261 AGTTGGTATT ACTGCAATGT CAAATGCTAA TAAACCTAGC GTTTCTCCTA TCAAAGTATT
1321 AAGTGAAAAA ATTGTCCAGA TATATCGTGA TGTGAAGCCG TTTGCTAGAG TAGCTGGTAT
1381 TGAAGTTCCT AGTGATCCTT TGCCTAATAG TGCATCTGTT GAGCAGATAC AGAATAAAAT
```

```
1441 GCAAGAATTA AATGATATAT TGGATGAGAT CAGAGATTCT TTTGACGGGT GTATTGGTGG

1501 TAATGCTTTC GCTAATCAGA TACAGTTGAA TTTTCGCATT CCGCAAGCAC AGCAGCAGGG

1561 GCAAGGGCAG CAACAGCAGC AAGCTCAAGC TACAGCGCAA GAAGCAGCAG CGGCAGCAGC

1621 TGTTAGGGTT TTAAATAACA ATGATCAGAT TATAAAGTTA TATAAAGATC TTGTTAAATT

1681 GAAGCGTCAT GCAGGAATTA AAAAGCTAT GGAAGAATTG GCTGCTCAAG ACGGAGGTTG

1741 TAATGGAGGT GGTGATAATA AGAAGAAGCG AGGAGCATCT GAAGACTCTG ATGCAGGAGG

1801 TGCTTCTAAA GGAGGGAAAG GCAAAGAAAC AAAAGAAACA GAGTTTGATC TGAGTATGAT

1861 TGTCGGCCAA GTTAAACTCT ATGCTGACTT ATTTACAACT GAATCATTCT CAATATATGC

1921 TGGTCTTGGT GCAGGGTTAG CTTATACTTC TGGAAAAATA GATGGTGTGG ACATTAAAGC

1981 TAATACTGGT ATGGTTGCAT CAGGAGCACT TGGTGTAGCA ATTAATGCTG CTGAGGGTGT

2041 GTATGTGGAC ATAGAAGGTA GTTATATGCA TTCATTCAGT AAAATAGAAG AGAAGTATTC

2101 AATAAATCCT CTTATGGCAA GTTTTGGTGT ACGCTATAAC TTC
```

Gilliam: Open Reading Frame (#556-#2127) (SEQ ID NO. 12) and Cloned Sequence (#796-#1899) is Bolded

```
ATGAAAAAATTATGTTAATTGCTAGTGCAATGTCTGCATTGTCATTGCC
GTTTTCAGCTAGTGCAATAGAATTGGGTGAGGAAGGAGGATTAGAGTGTG
GTCCTTACGGTAAAGTTGGAATCGTTGGAGGAATGATTACTGGTGCAGAA
TCTACTCGCTTGGATTCAACTGATTCTGAGGGAAAAAAACATTTGTCATT
AACAACTGGACTGCCATTTGGTGGTACATTAGCTGCGGGTATGACAATTG
CACCAGGATTTAGAGCAGAGCTAGGTGTTATGTACCTTAGAAATATAAGC
GCTGAGGTTGAAGTAGGTAAAGGCAAGGTAGATTCTAAAGGTGAGATAAA
GGCAGATTCTGGAGGTGGGACAGATACTCCTATACGTAAGCGGTTTAAAC
TTACACCACCTCAGCCTACTATAATGCCTATAAGTATAGCTGATCGTGAT
GTGGGGGTTGATACTGATATTCTTGCTCAAGCTGCTGCTGGGCAACCACA
GCTTACTGTTGAGCAGCGGGCTGCAGATAGGATTGCTTGGTTGAAGAATT
ATGCTGGTATTGACTATATGGTCCCAGATCCTCAGAATCCTAATGCTAGA
GTTATAAATCCTGTATTGTTAAATATTACTCAAGGGCCACCTAATGTACA
GCCTAGACCTCGGCAAAATCTTGACATACTTGACCATGGTCAGTGGAGAC
ATTTGGTAGTTGGTGTTACTGCATTGTCACATGCTAATAAACCTAGCGTT
ACTCCTGTCAAAGTATTAAGTGACAAAATTACTAAGATATATAGTGATAT
AAAGCCATTTGCTGATATAGCTGGTATTGATGTTCCTGATACTGGTTTGC
CTAATAGTGCATCTGTCGAACAGATACAGAGTAAAATGCAAGAATTAAAC
GATGTATTGGAAGACCTCAGAGATTCTTTTGATGGGTATATGGGTAATGC
TTTTGCTAATCAGATACAGTTGAATTTTGTCATGCCGCAGCAAGCACAGC
AGCAGCAGGGGCAAGGGCAGCAACAGCAAGCTCAAGCTACAGCGCAAGAA
GCAGTAGCAGCAGCAGCTGTTAGGCTTTTAAATGGCAATGATCAGATTGC
GCAGTTATATAAAGATCTTGTTAAATTGCAGCGTCATGCAGGAGTTAAGA
AAGCCATGGAAAAATTAGCTGCCCAACAAGAAGAAGATGCAAAGAATCAA
GGTGAAGGTGACTGTAAGCAGCAACAAGGAGCATCTGAAAAATCTAAAGA
AGGAAAAGGCAAAGAAACAGAGTTTGATCTGAGTATGATTGTTGGCCAAG
TTAAACTCTATGCTGACTTATTTACAACTGAATCATTCTCAATATATGCT
GGTGTTGGTGCAGGGTTAGCTCATACTTATGGAAAAATAGATGATAAGGA
TATTAAAGGGCATACAGGCATGGTTGCATCAGGAGCACTTGGTGTAGCAA
TTAATGCTGCTGAGGGTGTATATGTGGACTTAGAAGGTAGTTATATGCAC
TCATTCAGTAAAATAGAAGAGAAGTATTCAATAAATCCTCTTATGGCAAG
TGTAGGTGTACGCTATAACTTC
```

What is claimed is:

1. An assay for detecting antibody to scrub typhus comprising:
   a) Obtaining a sample from a subject; and
   b) Exposing the sample to at least one polypeptide, selected from the group consisting of: an isolated polypeptide consisting of SEQ ID NO: 4, an isolated polypeptide consisting of SEQ ID NO: 5, or a combination thereof, said polypeptide or polypeptides being the refolded expressed product or products of truncated non-fusion r56 genes from *Orientia tsutsugamushi*;
   c) Incubating said sample, wherein said antibody binds said at least one polypeptide forming a complex;
   d) Binding a detectable label to said complex wherein a detectable signal is produced;
   e) Detecting the signal, wherein the signal indicates the presence of said antibody.

2. The assay of claim 1, wherein said assay is selected from the group consisting of Elisa plates, dot-blot matrices, and hand held chromatographic and flow through assay devices.

3. An assay for detecting antibody to scrub typhus comprising:
   a) Obtaining a sample from a subject; and
   b) Exposing the sample to a combination of isolated polypeptides having the amino acids sequences set forth in SEQ ID NO:1, SEQ ID NO: 4, and SEQ ID NO: 5, said polypeptides being the refolded expressed product or products of truncated non-fusion r56 genes from *Orientia tsutsugamushi*;
   c) Incubating said sample, wherein said antibody binds said at least one polypeptide forming a complex;
   d) Binding a detectable label to said complex wherein a detectable signal is produced;
   e) Detecting the signal, wherein the signal indicates the presence of said antibody.

4. The assay of claim 1, wherein said assay is selected from the group consisting of Elisa plates, dot-blot matrices, and hand held chromatographic and flow through assay devices.

* * * * *

SEQUENCE LISTING

<160> NUMBER OF SEQ ID NOS: 3

<210> SEQ ID NO 1
<211> LENGTH: 378
<212> TYPE: PRT
<213> ORGANISM: Orientia tsutsugamushi

<400> SEQUENCE: 1

```
Met Thr Ile Ala Pro Gly Phe Arg Ala Glu Ile Gly Val Met Tyr Leu
  1               5                  10                  15
Thr Asn Ile Thr Ala Gln Val Glu Glu Gly Lys Val Lys Ala Asp Ser
             20                  25                  30
Val Gly Glu Thr Lys Ala Asp Ser Val Gly Gly Lys Asp Ala Pro Ile
         35                  40                  45
Arg Lys Arg Phe Lys Leu Thr Pro Pro Gln Pro Thr Ile Met Pro Ile
     50                  55                  60
Ser Ile Ala Val Arg Asp Phe Gly Ile Asp Ile Pro Asn Ile Pro Gln
 65                  70                  75                  80
Gln Gln Ala Gln Ala Ala Gln Pro Gln Leu Asn Asp Glu Gln Arg Ala
                 85                  90                  95
Ala Ala Arg Ile Ala Trp Leu Lys Asn Cys Ala Gly Ile Asp Tyr Arg
            100                 105                 110
Val Lys Asn Pro Asn Asp Pro Asn Gly Pro Met Val Ile Asn Pro Ile
        115                 120                 125
Leu Leu Asn Ile Pro Gln Gly Asn Pro Asn Pro Val Gly Asn Pro Pro
    130                 135                 140
Gln Pro Arg Ala Asn Pro Pro Ala Gly Phe Ala Ile His Asn His Glu
145                 150                 155                 160
Gln Trp Arg His Leu Val Val Gly Leu Ala Ala Leu Ser Asn Ala Asn
                165                 170                 175
Lys Pro Ser Ala Ser Pro Val Lys Val Leu Ser Asp Lys Ile Thr Gln
            180                 185                 190
Ile Tyr Ser Asp Ile Lys His Leu Ala Asp Ile Ala Gly Ile Asp Val
        195                 200                 205
Pro Asp Thr Ser Leu Pro Asn Ser Ala Ser Val Glu Gln Ile Gln Asn
    210                 215                 220
Lys Met Gln Glu Leu Asn Asp Leu Leu Glu Glu Leu Arg Glu Ser Phe
225                 230                 235                 240
Asp Gly Tyr Leu Gly Gly Asn Ala Phe Ala Asn Gln Ile Gln Leu Asn
                245                 250                 255
Phe Val Met Pro Gln Gln Ala Gln Gln Gln Gly Gln Gly Gln Gln Gln
            260                 265                 270
Gln Ala Gln Ala Thr Ala Gln Glu Ala Val Ala Ala Ala Val Arg
        275                 280                 285
Leu Leu Asn Gly Asn Asp Gln Ile Ala Gln Leu Tyr Lys Asp Leu Val
    290                 295                 300
Lys Leu Gln Arg His Ala Gly Ile Lys Lys Ala Met Glu Lys Leu Ala
305                 310                 315                 320
Ala Gln Gln Glu Glu Asp Ala Lys Asn Gln Gly Glu Gly Asp Cys Lys
                325                 330                 335
Gln Gln Gln Gly Thr Ser Glu Lys Ser Lys Gly Lys Asp Lys Glu
            340                 345                 350
Ala Glu Phe Asp Leu Ser Met Ile Val Gly Gln Val Lys Leu Tyr Ala
        355                 360                 365
Asp Val Met Ile Thr Glu Ser Val Ser Ile
    370                 375
```

<210> SEQ ID NO 2
<211> LENGTH: 36
<212> TYPE: DNA

-continued

```
<213> ORGANISM: Orientia tsutsugamushi

<400> SEQUENCE: 2
ttggctgcac atatgacaat cgctccagga tttaga                    36

<210> SEQ ID NO 3
<211> LENGTH: 48
<212> TYPE: DNA
<213> ORGANISM: Orientia tsutsugamushi

<400> SEQUENCE: 3
ctttctagaa gtataagcta acccggatcc aacaccagcc tatattga       48
```